(12) United States Patent
David et al.

(10) Patent No.: US 11,014,921 B2
(45) Date of Patent: May 25, 2021

(54) THERAPEUTIC COMPOUNDS AND METHODS OF USE THEREOF

(71) Applicant: Regents of the University of Minnesota, Minneapolis, MN (US)

(72) Inventors: Sunil A. David, Minneapolis, MN (US); Janardhan Banothu, Minneapolis, MN (US); Mallesh Beesu, Minneapolis, MN (US); Michael Brush, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 16/447,721

(22) Filed: Jun. 20, 2019

(65) Prior Publication Data

US 2019/0389854 A1 Dec. 26, 2019

Related U.S. Application Data

(60) Provisional application No. 62/687,638, filed on Jun. 20, 2018.

(51) Int. Cl.
| | | |
|---|---|---|
| *C07D 455/06* | (2006.01) | |
| *A61K 31/4745* | (2006.01) | |
| *A61K 47/64* | (2017.01) | |
| *G01S 13/91* | (2006.01) | |
| *G08G 5/00* | (2006.01) | |
| *H04B 7/06* | (2006.01) | |
| *H04B 7/08* | (2006.01) | |
| *H04B 7/26* | (2006.01) | |

(52) U.S. Cl.
CPC ........ *C07D 455/06* (2013.01); *A61K 31/4745* (2013.01); *A61K 47/646* (2017.08); *G01S 13/91* (2013.01); *G08G 5/0008* (2013.01); *H04B 7/0617* (2013.01); *H04B 7/086* (2013.01); *H04B 7/2606* (2013.01)

(58) Field of Classification Search
CPC . C07D 455/06; A61K 47/646; A61K 31/4745
See application file for complete search history.

(56) References Cited

PUBLICATIONS

Yegorova et al., 61A(1-2) Spectrochimica Acta, Part A: Molecular & Biomolecular Spectroscopy, p. 109-116 (2004) (vol. Date (2005)) (Year: 2004).*

Ukrainets, I.V., 42(9) Chem. Heterocyclic Compounds, 1208-1222 (2006) (Year: 2006).*
Alekscandrova, D.I., et al., 64(7) J. Anal. Chem., 705-713 (2009) (Year: 2009).*
Aleksandrova et al., 66(6) Acta Poloniae Pharmaceutica, 605-610 (2009) (Year: 2009).*
Ahmed, S , et al., "Assessing the Safety of Adjuvanted Vaccines", Sci Transl Med 3(93), 93rv2 (2011).
Campbell, J , "Development of the CpG Adjuvant 1018: A Case Study", Methods Molec Biol 1494, 15-27 (2017).
Hoffmann, J , et al., "Innate immunity", Curr Opin Immunol 25, 1-3 (2013).
Jackson, S , et al., "Immunogenicity of a two-dose investigational hepatitis B vaccine, HBsAg-1018, using a toll-like receptor 9 agonist adjuvant compared with a licensed hepatitis B vaccine in adults", Vaccine 36, 668-674 (2018).
Pandey, S , et al., "Microbial Sensing by Toll-Like Receptors and Intracellular Nucleic Acid Sensors", Cold Spring Harb Perspect Biol 7, a016246 (2014).
Plotkin, S , et al., "Vaccines: past, present and future", Nat Med 11(4 Suppl), S5-S11 (2005).
Plotkin, S , "Vaccines: the fourth century", Clin Vaccin Immunol 16, 1709-1719 (2009).
Tagliabue, A , et al., "Vaccine adjuvants: The dream becomes real", Hum Vaccin 4, 347-349 (2008).
Takeda, K , et al., "Toll-like receptors", Cliff Protoc Immunol 109, 14.12.1 (2015).

* cited by examiner

*Primary Examiner* — Timothy R Rozof
(74) *Attorney, Agent, or Firm* — Viksnins Harris Padys Malen LLP

(57) ABSTRACT

The invention provides a compound of formula I:

(I)

or a salt thereof, wherein $R^1$, $R^2$, and $R^3$ have any of the values described in the specification, as well as compositions comprising a compound of formula I. The compounds are useful as immunomodulating agents.

2 Claims, 2 Drawing Sheets

THERAPEUTIC COMPOUNDS AND METHODS OF USE THEREOF

CROSS-REFERENCE TO RELATED APPLICATIONS

This application claims the benefit of U.S. Provisional Application Ser. No. 62/687,638 filed Jun. 20, 2018. The entire content of the application referenced above is hereby incorporated by reference herein.

GOVERNMENT FUNDING

This invention was made with government support under HHSN272201400056C awarded by the National Institutes of Health. The government has certain rights in the invention.

BACKGROUND

The sustained decrease in mortality caused by infectious diseases is largely attributable to immunization, and vaccines continue to play an indispensable role in decreasing the burden of infectious diseases worldwide (Plotkin, S. A. Clin. Vaccin. *Immunol.* 2009, 16, 1709). The major categories of vaccines are those that contain live attenuated microbes, those that contain killed microbes, and those that contain one or more of an antigenic subunit (such as protein or polysaccharide) derived from the microbe (Plotkin, S. *A. Nat. Med.* 2005, 11, S5). Modern vaccines increasingly rely on well-defined, highly purified subunit and recombinant antigens, and often require the incorporation of appropriate immune potentiators (also termed adjuvants), along with the antigen. Adjuvants initiate early innate immune responses and thereby enhance immunogenicity, leading to more robust and long-lasting adaptive immune responses (Ahmed, S. S. et al. *Sci. Transl. Med.* 2011, 3, 93rv2).

Toll-like receptors (TLRs) are a family of pattern recognition receptors that serve as key sentinels of innate immune system. There are 10 TLRs in the human genome; these trans-membrane proteins recognize pathogen-associated molecular patterns that are broadly shared by pathogens but are sufficiently different so as to be distinguishable from host molecules (Takeda, K. *Curr. Protoc. Immunol.* 2015, 109, 14.12.1; Pandey, S. et al. *Cold Spring Harb. Perspect. Biol.* 2014, 7, a016246 and Hoffmann, J. et al. *Curr. Opin. Immunol.* 2013, 25, 1). The engagement of innate immune receptors plays a role in the action of many vaccine adjuvants such as mono-phosphoryl lipid A (TLR4 agonist) (Tagliabue, A. et al. *Hum. Vaccin.* 2008, 4, 347) and Adjuvant 1018 (TLR9 agonist) (Jackson, S. et al. *Vaccine* 2018, 36, 668 and Campbell, J. D. *Methods Molec. Biol.* 2017, 1494, 15), highlighting the importance and utility of innate immune stimulatory molecules in the design and development of novel vaccines.

There is currently a need for compounds possessing TLR2 activity, and bearing functional groups that can allow chemical transformation, including conjugation to biomolecules.

SUMMARY

This invention provides novel compounds possessing TLR2 activity, and bearing functional groups that allow chemical transformation, including conjugation to biomolecules. Accordingly, the invention provides a compound of the invention, which is a compound of formula I:

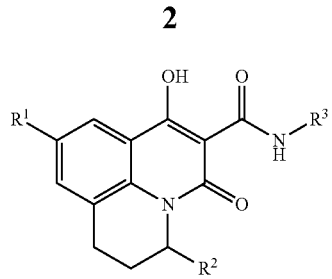

or a salt thereof, wherein:
$R^1$ is halogen;
$R^2$ is $(C_1-C_6)$alkyl that is optionally substituted with one or more groups independently selected from halogen;
$R^3$ is aryl, heteroaryl, cycloalkyl, heterocycle, or $(C_1-C_6)$alkyl that is substituted with aryl, heteroaryl, cycloalkyl, heterocycle, wherein any aryl, heteroaryl, cycloalkyl or heterocycle is optionally substituted with one or more groups independently selected from alkyl, hydroxy, halogen, aryl, heteroayl, —$NR^aR^b$, —$C(=O)NR^aR^b$, —$CF_3$, $(C_2-C_6)$alkanoyloxy, $(C_1-C_6)$alkanoyl, $(C_1-C_6)$alkoxycarbonyl, and $(C_1-C_6)$alkoxy;
each $R^a$ and $R^b$ is independently selected from the group consisting of H and $(C_1-C_6)$alkyl; or $R^a$ and $R^b$ together with the nitrogen to which they are attached form a aziridino, azetidino, morpholino, piperazino, pyrrolidino, imidazole, or piperidino.

The invention provides a pharmaceutical composition comprising a compound of formula I, or a pharmaceutically acceptable salt thereof, and a pharmaceutically acceptable excipient.

The invention provides a method for stimulating immune activity in an animal comprising administering a compound of formula I, or a pharmaceutically acceptable salt thereof, to the animal.

The invention provides a method for immunizing a host comprising, administering to the host, 1) an antigen and 2) a compound of formula I, or a pharmaceutically acceptable salt thereof. The invention provides a compound of formula I, or a pharmaceutically acceptable salt thereof, for use in medical therapy.

The invention provides a compound of formula I, or a pharmaceutically acceptable salt thereof, for stimulating immune activity.

The invention provides a use of a compound of formula I, or a pharmaceutically acceptable salt thereof, to prepare a medicament for stimulating immune activity in an animal.

The invention provides a composition comprising an antigen and a compound of formula I, or a pharmaceutically acceptable salt thereof.

The invention provides a self-adjuvanting vaccine comprising a compound of formula I, or a pharmaceutically acceptable salt thereof linked to an antigen.

Certain compounds of the invention may be particularly useful because they may be selective for TLR2 over other toll-like receptors, such as, for example, TLR8.

Certain compounds of the invention may be particularly useful because they selectively activate TLR2 or alternate receptors (such as the inflammasome) in triggering the productions of specific cytokines.

DETAILED DESCRIPTION

Figures 1A, 1B:
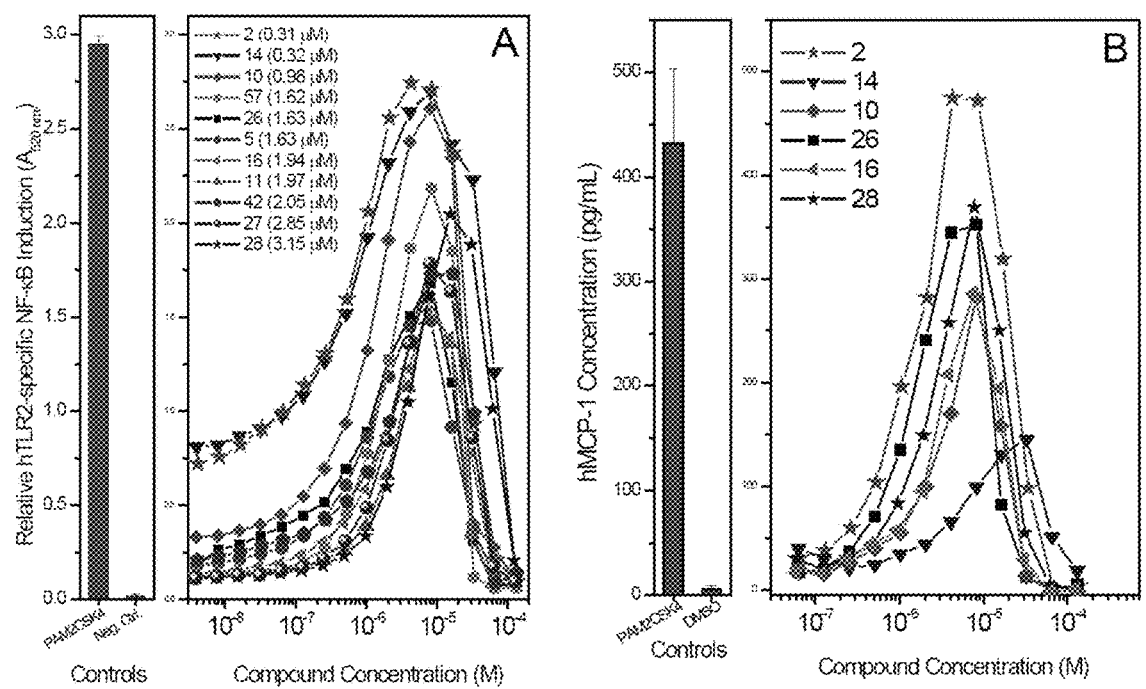
FIG. 1A-1B shows 1A) Human TLR2-specific agonistic potencies ($EC_{50}$ values) of active analogues in primary screens (reporter gene assay) 1B). Human MCP-1 induction in human TLR2-expressing cells by select analogues. PAM2CSK4 (100 ng/mL) was used as positive control in both assays and the data shown are means of quadruplicates
Figure 2:
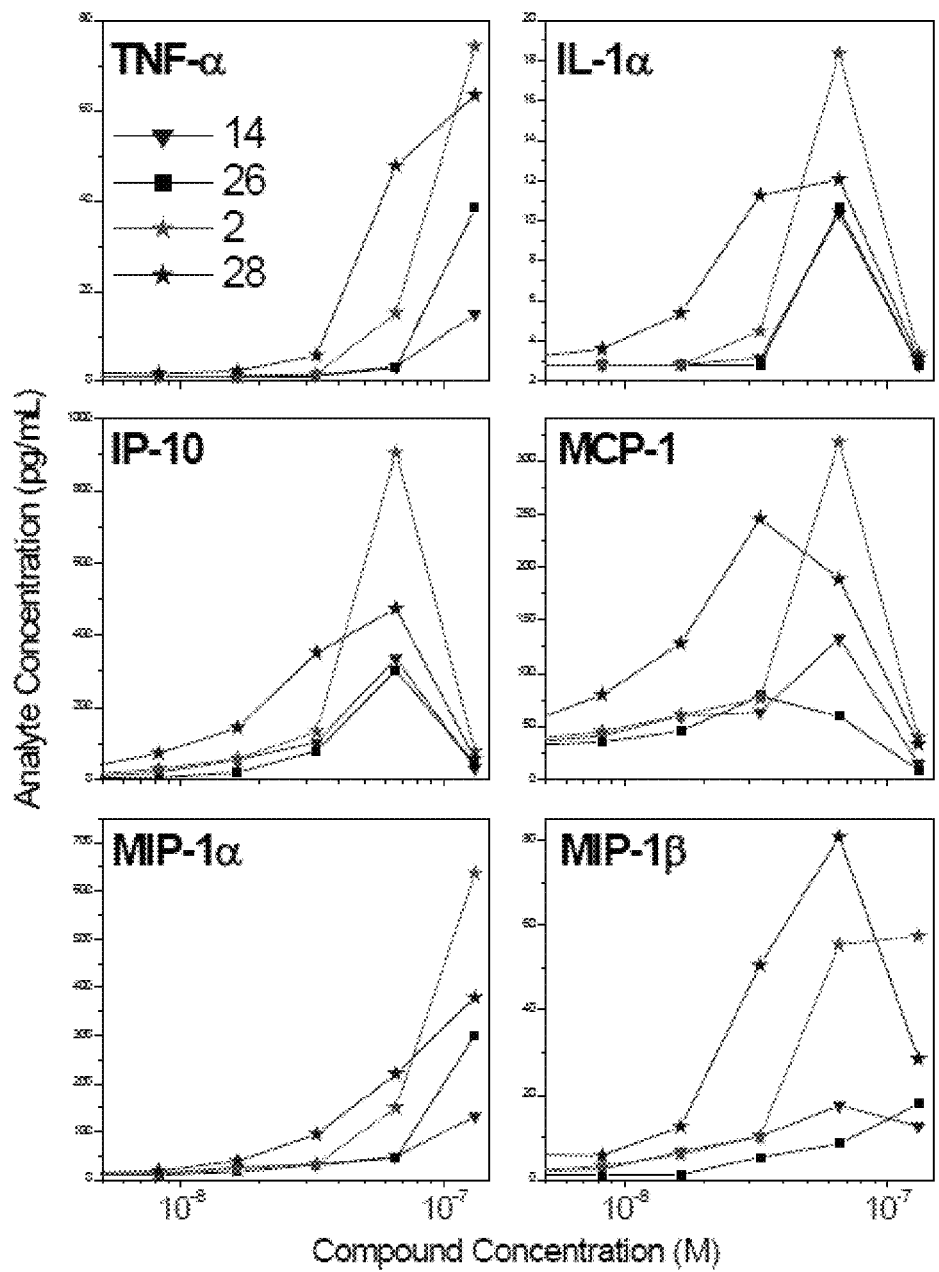
FIG. 2 shows the dose-response profiles of cytokine and chemokine induction in THP-1 cells and the data shown are means of triplicates.

The following definitions are used, unless otherwise described: halo or halogen is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include $(C_1-C_8)$alkyl, $(C_2-C_8)$alkyl, $C_1-C_6)$alkyl, $(C_2-C_6)$alkyl and $(C_3-C_6)$alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkoxy" refers to an alkyl groups attached to the remainder of the molecule via an oxygen atom ("oxy").

The term "cycloalkyl" refers to a saturated or partially unsaturated (non-aromatic) all carbon ring having 3 to 8 carbon atoms (i.e., $(C_3-C_8)$carbocycle). The term also includes multiple condensed, saturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 3 to 15 carbon atoms, about 6 to 15 carbon atoms, or 6 to 12 carbon atoms such as bicyclo[3.1.0] hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1] heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-10 membered heterocycle. In one embodiment the term heterocycle includes a 3-8 membered heterocycle. In one embodiment the term heterocycle includes a 3-7 membered heterocycle. In one embodiment the term heterocycle includes a 3-6 membered heterocycle. In one embodiment the term heterocycle includes a 4-6 membered heterocycle. In one embodiment the term heterocycle includes a 3-10 membered monocyclic or bicyclic heterocycle comprising 1 to 4 heteroatoms. In one embodiment the term heterocycle includes a 3-8 membered monocyclic or bicyclic heterocycle comprising 1 to 3 heteroatoms. In one embodiment the term heterocycle includes a 3-6 membered monocyclic heterocycle comprising 1 to 2 heteroatoms. In one embodiment the term heterocycle includes a 4-6 membered monocyclic heterocycle comprising 1 to 2 heteroatoms. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl"

includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "alkoxycarbonyl" as used herein refers to a group (alkyl)-O—C(=O)—, wherein the term alkyl has the meaning defined herein.

The term "alkanoyloxy" as used herein refers to a group (alkyl)-C(=O)—O—, wherein the term alkyl has the meaning defined herein.

As used herein, the term "heteroatom" is meant to include oxygen (O), nitrogen (N), sulfur (S) and silicon (Si).

As used herein a wavy line "〰" that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^1$ is flourine.
A specific value for $R^2$ is methyl.
A specific value for $R^3$ is:

2

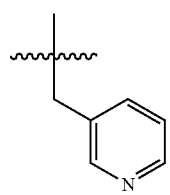

3

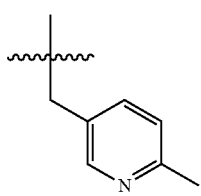

-continued

4

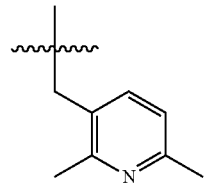

5

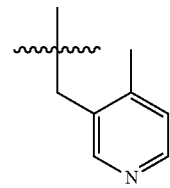

6

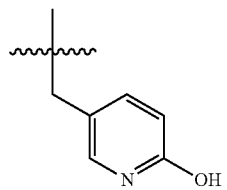

7

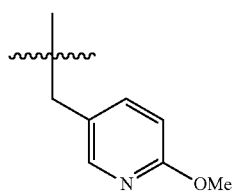

8

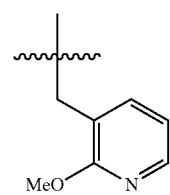

9

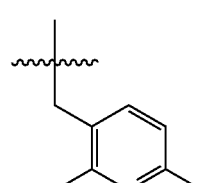

10

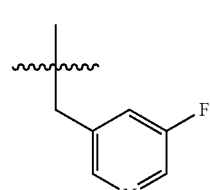

11

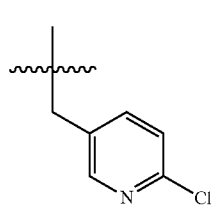

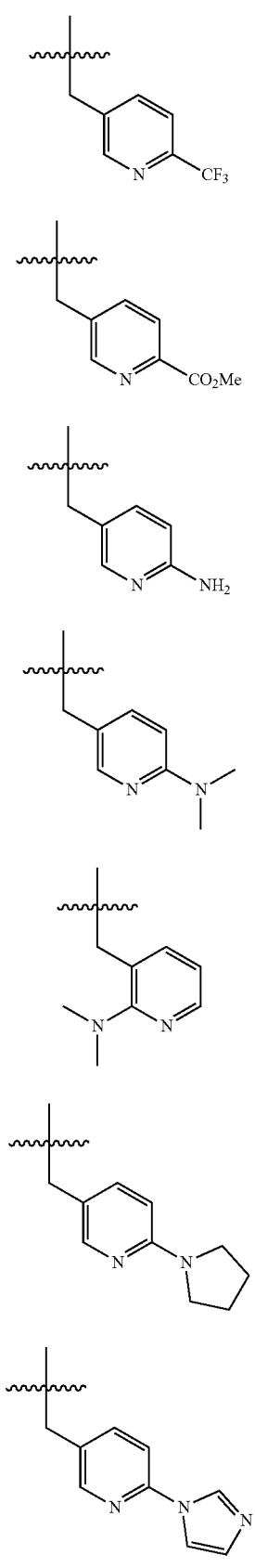
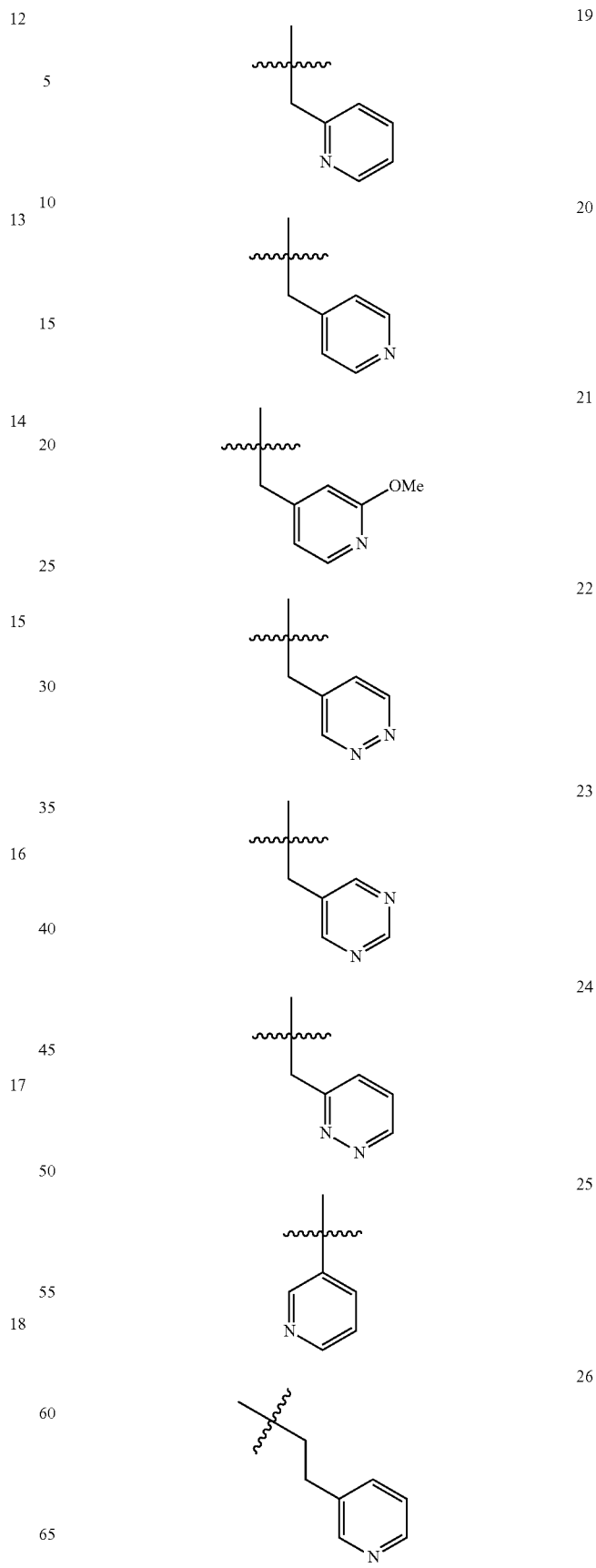

-continued
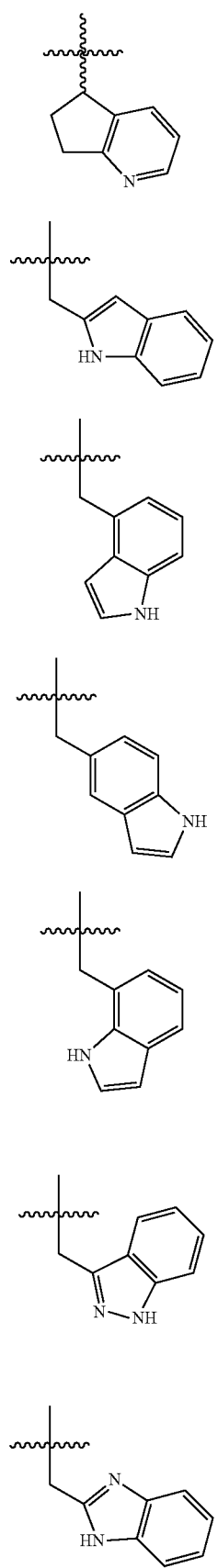
-continued
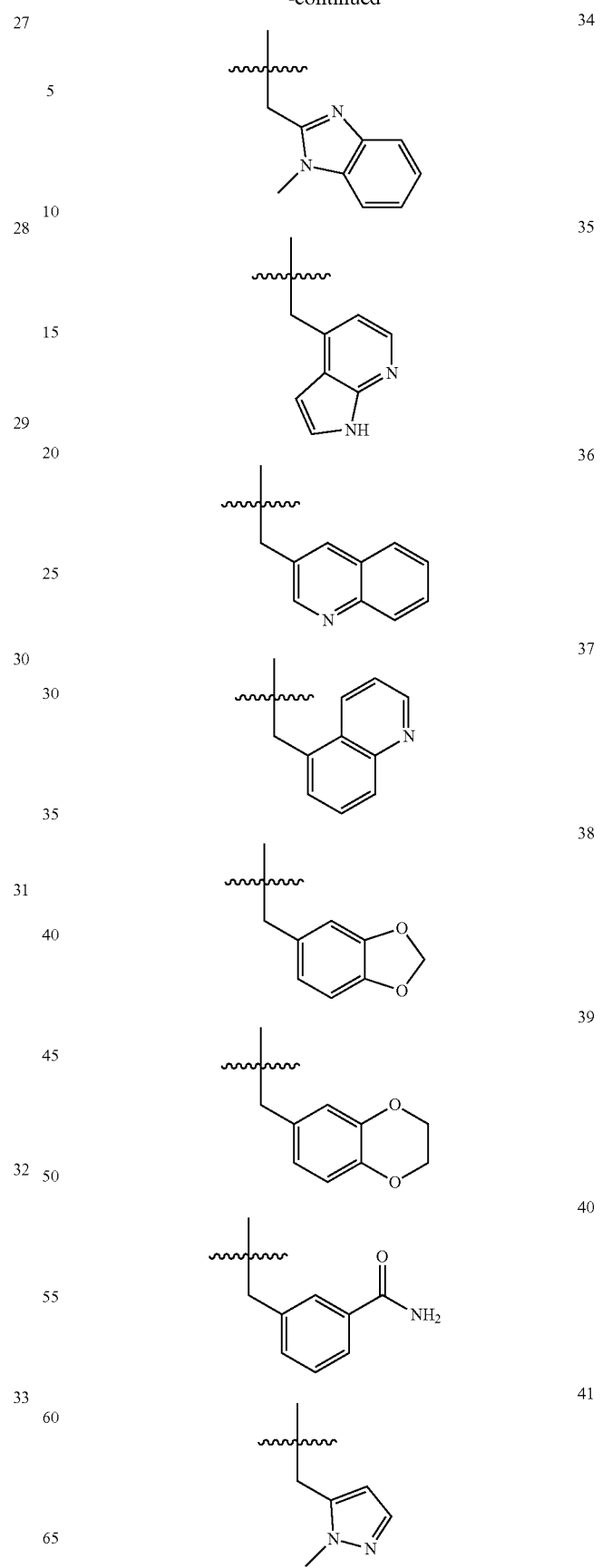

42
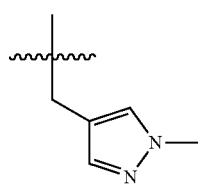
43
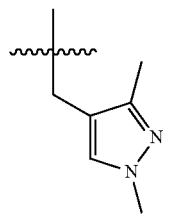
44
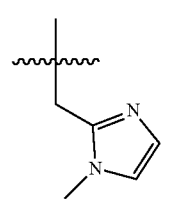
45
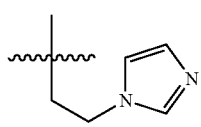
46
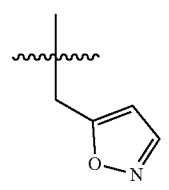
47
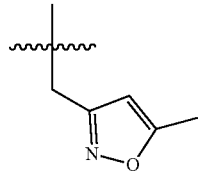
48
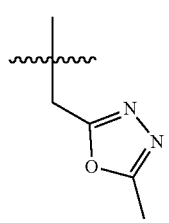
49
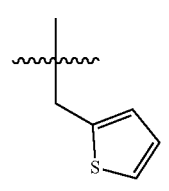
50
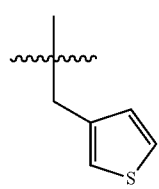
51
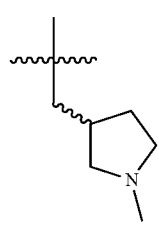
52
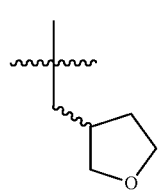
53
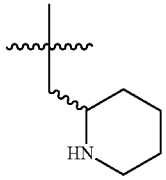
54
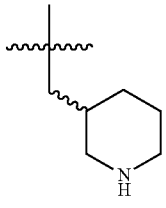
55
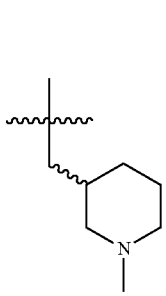
56
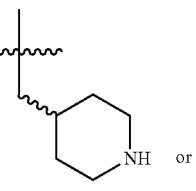 or -continued

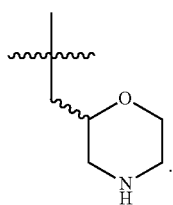
57

In one embodiment R³ is not pyridyl, when R¹ is F and R² is methyl.

In one embodiment R³ is not pyridyl.

In one embodiment R³ is not pyridyl, pyrazinyl, or pyrimidinyl.

In one embodiment R³ is not a 6-membered nitrogen containing heteroaryl.

In one embodiment, R³ is not a 6-membered heteroaryl.

In one embodiment, R³ is aryl, heteroaryl, cycloalkyl, heterocycle, or (C₁-C₆)alkyl that is substituted with aryl, heteroaryl, cycloalkyl, heterocycle.

In one embodiment, R³ is (C₁-C₆)alkyl that is substituted with aryl, heteroaryl, cycloalkyl, heterocycle.

In one embodiment, R³ is (C₁-C₆)alkyl that is substituted with aryl, cycloalkyl, heterocycle.

In one embodiment, R³ is aryl, heteroaryl, cycloalkyl, heterocycle.

In one embodiment, R³ is selected from the group consisting of:

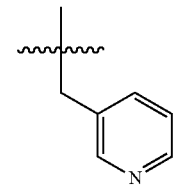
2

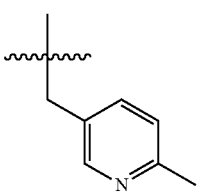
3

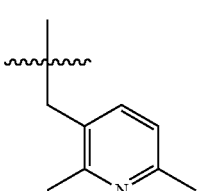
4

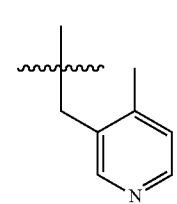
5

-continued

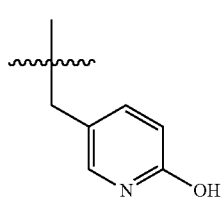
6

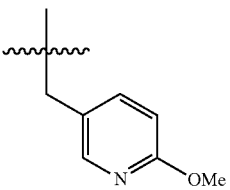
7

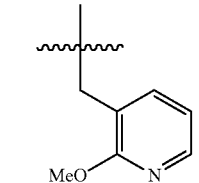
8

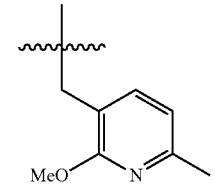
9

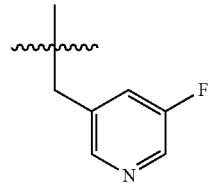
10

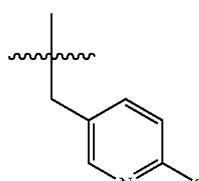
11

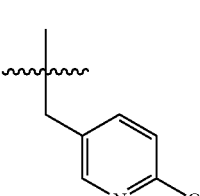
12

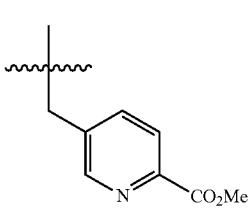
13

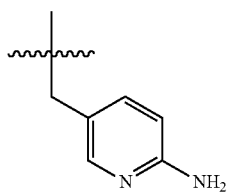

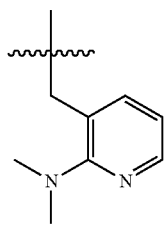

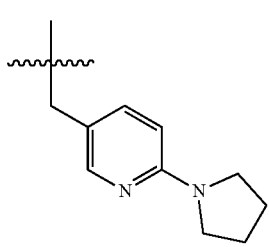

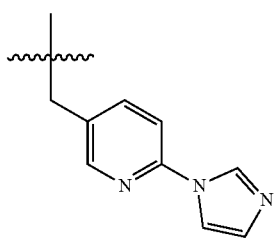

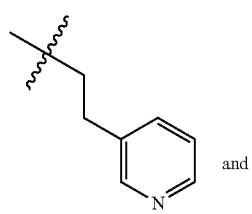

and

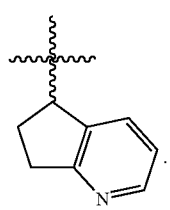

In one embodiment, $R^3$ is $(C_1\text{-}C_6)$alkyl that is substituted with:

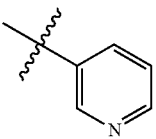 or 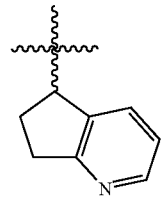

that is optionally substituted with one or more groups independently selected from alkyl, hydroxy, halogen, aryl, heteroayl, —NR$^a$R$^b$, —C(=O)NR$^a$R$^b$, —CF$_3$, $(C_2\text{-}C_6)$alkanoyloxy, $(C_1\text{-}C_6)$alkanoyl, $(C_1\text{-}C_6)$alkoxycarbonyl, and $(C_1\text{-}C_6)$alkoxy.

In one embodiment, $R^3$ is $(C_1\text{-}C_6)$alkyl that is substituted with:

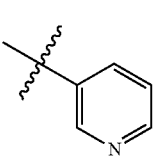 or 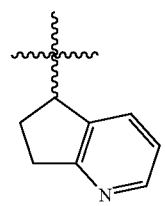

that is optionally substituted with one or more groups independently selected from alkyl, hydroxy, halogen, —NR$^a$R$^b$, —C(=O)NR$^a$R$^b$, —CF$_3$, $(C_1\text{-}C_6)$alkoxycarbonyl, and $(C_1\text{-}C_6)$alkoxy.

In one embodiment, $R^3$ is $(C_1\text{-}C_6)$alkyl that is substituted with:

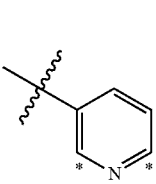 or 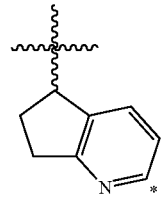

that is optionally substituted with one or more groups independently selected from alkyl, hydroxy, halogen, aryl, heteroayl, —NR$^a$R$^b$, —C(=O)NR$^a$R$^b$, —CF$_3$, $(C_2\text{-}C_6)$alkanoyloxy, $(C_1\text{-}C_6)$alkanoyl, $(C_1\text{-}C_6)$alkoxycarbonyl, and $(C_1\text{-}C_6)$alkoxy, at a carbon or carbons other than a carbon marked *.

In one embodiment, $R^3$ is $(C_1\text{-}C_6)$alkyl that is substituted with:

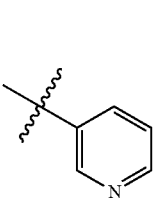 or 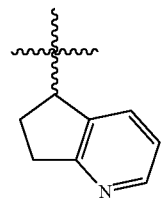

that is optionally substituted with one or more groups independently selected from methyl, ethyl, halo, —CF$_3$, methoxycarbonyl, and methoxy.

In one embodiment, the invention provides a compound of formula (I), which is a compound of formula (Ia):

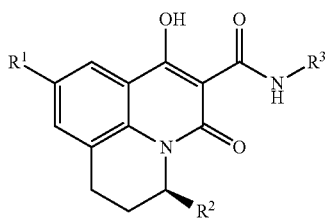

(Ia)

or a salt thereof, wherein R¹, R², and R³ have any of the values defined herein.

In one embodiment, the invention provides a compound of formula (I), which is a compound of formula (Ib):

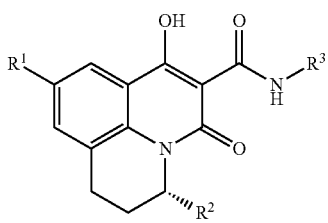

(Ib)

or a salt thereof, wherein R¹, R², and R³ have any of the values defined herein.

In one embodiment the invention provides a compound of formula (I) or a salt thereof, wherein:

R¹ is halogen;

R² is $(C_1-C_6)$alkyl that is optionally substituted with one or more groups independently selected from halogen;

R³ is aryl, heteroaryl, cycloalkyl, heterocycle, or $(C_1-C_6)$ alkyl that is substituted with aryl, heteroaryl, cycloalkyl, heterocycle, wherein any aryl, heteroaryl, cycloalkyl or heterocycle is optionally substituted with one or more groups independently selected from $(C_1-C_6)$alkyl, hydroxy, halogen, aryl, heteroayl, —NR$^a$R$^b$, —C(=O)NR$^a$R$^b$, —CF$_3$, $(C_2-C_6)$alkanoyloxy, $(C_1-C_6)$alkanoyl and $(C_1-C_6)$ alkoxy; and each R$^a$ and R$^b$ is independently selected from the group consisting of H and $(C_1-C_6)$alkyl; or R$^a$ and R$^b$ together with the nitrogen to which they are attached form a aziridino, azetidino, morpholino, piperazino, pyrrolidino or piperidino.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Example 1. Procedure for the Synthesis of Compound 1

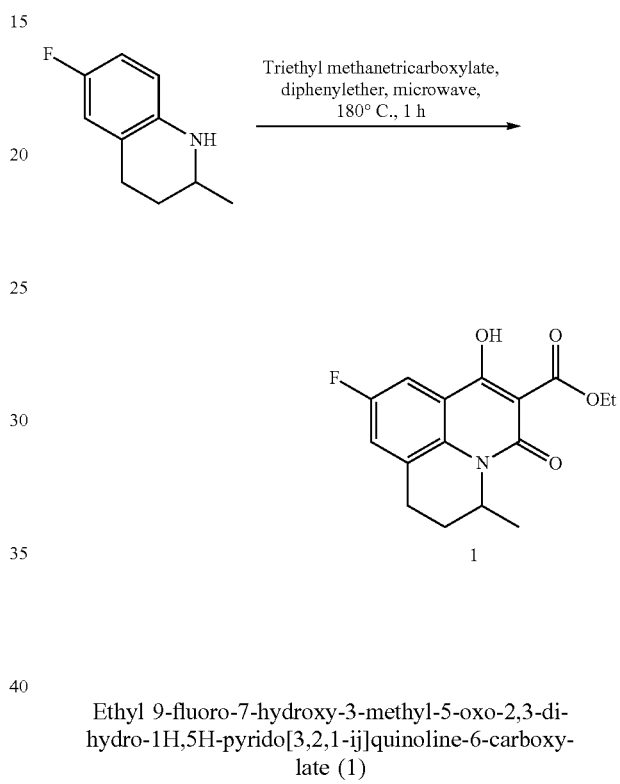

Ethyl 9-fluoro-7-hydroxy-3-methyl-5-oxo-2,3-dihydro-1H,5H-pyrido[3,2,1-ij]quinoline-6-carboxylate (1)

To a solution of 6-fluoro-2-methyl-1,2,3,4-tetrahydroquinoline (330.42 mg, 2 mmol) in anhydrous diphenyl ether (3 mL) was added triethyl methanetricarboxylate (466.58 L, 2.2 mmol). The reaction mixture was heated in a sealed vial at 180° C. for 1 h under microwave irradiation. The reaction mixture was cooled to room temperature, diluted with water and extracted with ethyl acetate (3×30 mL). The combined organic layer was dried over $Na_2SO_4$ and concentrated under reduced pressure, and the crude material was purified by flash chromatography (30% EtOAc/hexanes) to obtain the compound 1 as yellow solid (440 mg, 72%). $^1$H NMR (500 MHz, Chloroform-d) δ 14.10 (s, 1H), 7.68 (dd, J=8.6, 2.4 Hz, 1H), 7.24-7.18 (m, 1H), 5.35-5.23 (m, 1H), 4.61-4.41 (m, 2H), 3.22-3.08 (m, 1H), 2.84 (dd, J=16.7, 4.0 Hz, 1H), 2.11-2.02 (m, 1H), 1.99-1.88 (m, 1H), 1.49 (t, J=7.1 Hz, 3H), 1.28 (d, J=6.6 Hz, 3H). $^{13}$C NMR (126 MHz, CDCl$_3$) δ 172.76, 170.79 (d, J=2.52 Hz), 158.50, 157.15 (d, J=243.18 Hz), 134.09, 126.73 (d, J=7.56 Hz), 121.79 (d, J=23.94 Hz), 115.94 (d, J=8.82 Hz), 108.71 (d, J=22.68 Hz), 98.68, 62.59, 45.53, 25.86, 23.09, 17.98, 14.36. MS (ESI-TOF) for $C_{16}H_{16}FNO_4$ [M+H]$^+$ calculated 306.1136; found, 306.1142.

Example 2. Procedure for the Synthesis of Compound 2

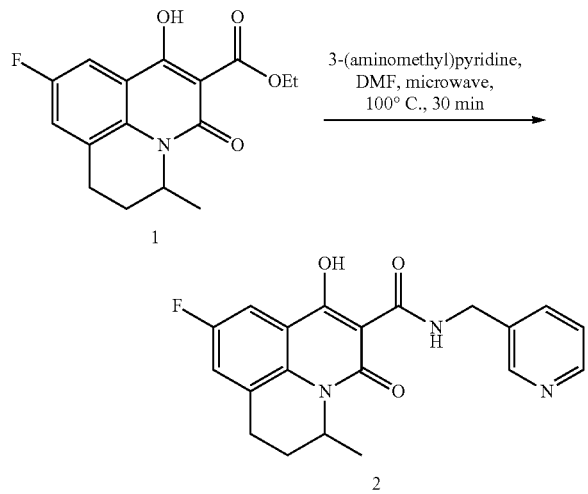

9-Fluoro-7-hydroxy-3-methyl-5-oxo-N-(pyridin-3-ylmethyl)-2,3-dihydro-1H,5H-pyrido[3,2,1-ij]quinoline-6-carboxamide (2)

To a solution of compound 1 (30.53 mg, 0.1 mmol) in anhydrous DMF (1 mL) was added 3-(aminomethyl)pyridine (12.22 µL, 0.12 mmol), and then heated in a sealed vial at 100° C. for 30 min under microwave irradiation. The solvent was removed under reduced pressure and the residue was purified by flash chromatography (30% EtOAc/hexanes) to obtain the compound 2 as a white solid (32 mg, 87%). $^1$H NMR (500 MHz, DMSO-$d_6$) δ 10.84 (t, J=6.0 Hz, 1H), 8.60 (d, J=1.7 Hz, 1H), 8.49 (dd, J=4.8, 1.6 Hz, 1H), 7.81-7.76 (m, 1H), 7.64-7.55 (m, 2H), 7.41-7.36 (m, 1H), 5.14-5.05 (m, 1H), 4.69-4.57 (m, 2H), 3.17-3.04 (m, 1H), 2.96-2.88 (m, 1H), 2.11-2.03 (m, 1H), 1.94-1.84 (m, 1H), 1.21 (d, J=6.6 Hz, 3H). $^{13}$C NMR (126 MHz, DMSO-$d_6$): δ 171.07, 170.57 (d, J=3.78 Hz), 160.73, 157.14 (d, J=241.92 Hz), 149.54, 148.94, 135.93, 134.38, 132.95, 128.60 (d, J=8.82 Hz), 124.13, 121.94 (d, J=23.94 Hz), 116.51 (d, J=8.82 Hz), 107.58 (d, J=22.68 Hz), 97.08, 45.93, 25.27, 22.54, 18.06. MS (ESI-TOF) for $C_{20}H_{18}FN_3O_3[M+H]^+$ calculated 368.1405; found, 368.1463.

Example 3. Procedure for the Synthesis of Compound 3-57

Compounds 3-8, 10-12, 14-26, 28-33, 35, 37-45, 47-52, 55 and N-Boc protected intermediates for compounds 53, 54, 56 were synthesized similarly as compound 2. Compound 13, 27, 34, 36, 46 were synthesized similarly as compound 9. Compound 54, 56 and 57 were synthesized similarly as compound 53.

9-Fluoro-7-hydroxy-3-methyl-N-((6-methylpyridin-3-yl)methyl)-5-oxo-2,3-dihydro-1H,5H-pyrido[3,2,1-ij]quinoline-6-carboxamide (3)

(6-Methylpyridin-3-yl)methanamine (14.66 mg, 0.12 mmol) was used as reagent. White solid (31 mg, 81%). $^1$H NMR (500 MHz, Chloroform-d) δ 16.70 (s, 1H), 10.81 (t, J=5.2 Hz, 1H), 8.51 (d, J=2.0 Hz, 1H), 7.74-7.69 (m, 1H), 7.61 (dd, J=8.0, 2.3 Hz, 1H), 7.24-7.20 (m, 1H), 7.14 (d, J=8.0 Hz, 1H), 5.28-5.17 (m, 1H), 4.69-4.54 (m, 2H), 3.22-3.10 (m, 1H), 2.92-2.82 (m, 1H), 2.54 (s, 3H), 2.11-2.04 (m, 1H), 2.03-1.92 (m, 1H), 1.28 (d, J=6.7 Hz, 3H). $^{13}$C NMR (126 MHz, CDCl$_3$) δ 171.19, 170.94 (d, J=3.78 Hz), 161.47, 157.83, 157.49 (d, J=243.18 Hz), 148.83, 136.13, 132.55, 130.48, 127.01 (d, J=6.30 Hz), 123.36, 121.32 (d, J=23.94 Hz), 117.41 (d, J=8.82 Hz), 108.60 (d, J=23.94 Hz), 97.45, 45.76, 40.49, 25.81, 24.30, 22.99, 18.08. MS (ESI-TOF) for $C_{21}H_{20}FN_3O_3[M+H]^+$ calculated 382.1561; found, 382.1546.

N-((2,6-Dimethylpyridin-3-yl)methyl)-9-fluoro-7-hydroxy-3-methyl-5-oxo-2,3-dihydro-1H,5H-pyrido[3,2,1-ij]quinoline-6-carboxamide (4)

(2,6-Dimethylpyridin-3-yl)methanamine (16.34 mg, 0.12 mmol) was used as reagent. White solid (27 mg, 68%). $^1$H NMR (500 MHz, Chloroform-d) δ 16.72 (s, 1H), 10.75 (t, J=5.0 Hz, 1H), 7.75-7.69 (m, 1H), 7.51 (d, J=7.8 Hz, 1H), 7.24-7.19 (m, 1H), 6.98 (d, J=7.8 Hz, 1H), 5.27-5.19 (m, 1H), 4.69-4.52 (m, 2H), 3.23-3.11 (m, 1H), 2.92-2.84 (m, 1H), 2.59 (s, 3H), 2.51 (s, 3H), 2.12-2.04 (m, 1H), 2.03-1.93 (m, 1H), 1.28 (d, J=6.7 Hz, 3H). $^{13}$C NMR (126 MHz, CDCl$_3$) δ 171.10, 170.96 (d, J=2.52 Hz), 161.51, 157.50 (d, J=243.18 Hz), 156.91, 156.04, 136.56, 132.54, 127.83, 127.01 (d, J=6.30 Hz), 121.32 (d, J=23.94 Hz), 121.04, 117.44 (d, J=8.82 Hz), 108.60 (d, J=22.68 Hz), 97.43, 45.75, 40.46, 25.80, 24.32, 23.00, 22.29, 18.09. MS (ESI-TOF) for $C_{22}H_{22}FN_3O_3[M+H]^+$ calculated 396.1718; found, 396.1799.

9-Fluoro-7-hydroxy-3-methyl-N-((4-methylpyridin-3-yl)methyl)-5-oxo-2,3-dihydro-1H,5H-pyrido[3,2,1-ij]quinoline-6-carboxamide (5)

(4-Methylpyridin-3-yl)methanamine (14.66 mg, 0.12 mmol) was used as reagent. White solid (30 mg, 79%). $^1$H NMR (500 MHz, Chloroform-d) δ 16.68 (s, 1H), 10.74 (s, 1H), 8.54 (s, 1H), 8.42 (d, J=4.9 Hz, 1H), 7.75-7.67 (m, 1H), 7.24-7.19 (m, 1H), 7.12 (d, J=5.0 Hz, 1H), 5.27-5.16 (m, 1H), 4.74-4.55 (m, 2H), 3.23-3.09 (m, 1H), 2.92-2.82 (m, 1H), 2.42 (s, 3H), 2.11-2.04 (m, 1H), 2.02-1.92 (m, 1H), 1.27 (d, J=6.7 Hz, 3H). $^{13}$C NMR (126 MHz, CDCl$_3$) δ 171.01, 170.95 (d, J=2.52 Hz), 161.49, 157.51 (d, J=244.44 Hz), 149.84, 149.31, 146.03, 132.56, 131.63, 127.02 (d, J=6.30 Hz), 125.56, 121.35 (d, J=23.94 Hz), 117.41 (d, J=8.82 Hz), 108.61 (d, J=22.68 Hz), 97.42, 45.76, 38.86, 25.80, 22.99, 18.87, 18.08. MS (ESI-TOF) for $C_{21}H_{20}FN_3O_3[M+H]^+$ calculated 382.1561; found, 382.1582.

9-Fluoro-7-hydroxy-N-((6-hydroxypyridin-3-yl)methyl)-3-methyl-5-oxo-2,3-dihydro-1H,5H-pyrido[3,2,1-ij]quinoline-6-carboxamide (6)

5-Aminomethy-1H-pyridin-2-one hydrobromide (24.61 mg, 0.12 mmol) was used as reagent. White solid (25 mg, 65%). $^1$H NMR (500 MHz, DMSO-$d_6$) δ 11.51 (s, 1H), 10.64 (t, J=5.5 Hz, 1H), 7.64-7.53 (m, 2H), 7.51-7.46 (m, 1H), 7.39 (s, 1H), 6.33 (d, J=9.4 Hz, 1H), 5.13-5.01 (m, 1H), 4.40-4.23 (m, 2H), 3.19-3.02 (m, 1H), 2.99-2.86 (m, 1H), 2.12-2.01 (m, 1H), 1.95-1.83 (m, 1H), 1.20 (d, J=6.5 Hz, 3H). $^{13}$C NMR (126 MHz, DMSO-$d_6$) δ 170.38, 170.14 (d, J=2.52 Hz), 161.83, 160.25, 156.66 (d, J=240.66 Hz), 141.78, 134.38, 132.44, 128.10 (d, J=7.56 Hz), 121.40 (d, J=23.94 Hz), 120.11, 116.09 (d, J=8.82 Hz), 114.81, 107.08 (d, J=22.68 Hz), 96.55, 45.43, 24.82, 22.07, 17.58. MS (ESI-TOF) for $C_{20}H_{18}FN_3O_4[M+H]^+$ calculated 384.1354; found, 384.1423.

9-Fluoro-7-hydroxy-N-((6-methoxypyridin-3-yl) methyl)-3-methyl-5-oxo-2,3-dihydro-1H,5H-pyrido [3,2,1-ij]quinoline-6-carboxamide (7)

(6-Methoxypyridin-3-yl)methanamine (16.58 mg, 0.12 mmol) was used as reagent. White solid (28 mg, 70%). $^1$H NMR (500 MHz, Chloroform-d) δ 16.76 (s, 1H), 10.75 (s, 1H), 8.17 (d, J=2.0 Hz, 1H), 7.75-7.68 (m, 1H), 7.62 (dd, J=8.5, 2.5 Hz, 1H), 7.24-7.18 (m, 1H), 6.73 (d, J=8.5 Hz, 1H), 5.26-5.17 (m, 1H), 4.64-4.49 (m, 2H), 3.92 (s, 3H), 3.21-3.10 (m, 1H), 2.92-2.82 (m, 1H), 2.11-2.03 (m, 1H), 2.01-1.92 (m, 1H), 1.27 (d, J=6.7 Hz, 3H). $^{13}$C NMR (126 MHz, CDCl$_3$) δ 171.09, 170.96 (d, J=2.52 Hz), 163.84, 161.46, 157.49 (d, J=243.18 Hz), 146.39, 138.88, 132.54, 127.00 (d, J=7.56 Hz), 126.34, 121.29 (d, J=23.94 Hz), 117.45 (d, J=8.82 Hz), 111.19, 108.59 (d, J=23.94 Hz), 97.44, 53.63, 45.74, 40.17, 25.81, 22.99, 18.08. MS (ESI-TOF) for $C_{21}H_{20}FN_3O_4[M+H]^+$ calculated 398.1511; found, 398.1573.

9-Fluoro-7-hydroxy-N-((2-methoxypyridin-3-yl) methyl)-3-methyl-5-oxo-2,3-dihydro-1H,5H-pyrido [3,2,1-ij]quinoline-6-carboxamide (8)

(2-Methoxypyridin-3-yl)methanamine (16.58 mg, 0.12 mmol) was used as reagent. Yellow solid (35 mg, 88%). $^1$H NMR (500 MHz, Chloroform-d) δ 16.86 (s, 1H), 10.80 (t, J=5.3 Hz, 1H), 8.09 (dd, J=5.0, 1.9 Hz, 1H), 7.75-7.67 (m, 1H), 7.63-7.56 (m, 1H), 7.24-7.18 (m, 1H), 6.90-6.83 (m, 1H), 5.30-5.22 (m, 1H), 4.68-4.52 (m, 2H), 4.02 (s, 3H), 3.23-3.10 (m, 1H), 2.93-2.82 (m, 1H), 2.13-2.05 (m, 1H), 2.02-1.93 (m, 1H), 1.29 (d, J=6.7 Hz, 3H). $^{13}$C NMR (126 MHz, CDCl$_3$) δ 171.22, 170.97 (d, J=2.52 Hz), 161.94, 161.48, 157.46 (d, J=244.44 Hz), 145.89, 137.26, 132.57, 126.94 (d, J=7.56 Hz), 121.21 (d, J=23.94 Hz), 120.42, 117.48 (d, J=8.82 Hz), 116.90, 108.58 (d, J=22.68 Hz), 97.55, 53.66, 45.67, 38.12, 25.82, 23.01, 18.11. MS (ESI-TOF) for $C_{21}H_{20}FN_3O_4[M+H]^+$ calculated 398.1511; found, 398.1566.

9-Fluoro-7-hydroxy-N-((2-methoxy-4,6-dimethylpyridin-3-yl)methyl)-3-methyl-5-oxo-2,3-dihydro-1H,5H-pyrido[3,2,1-ij]quinoline-6-carboxamide (9)

To a solution of compound 1 (30.53 mg, 0.1 mmol) in anhydrous DMF (1 mL) were added (2-methoxy-4,6-dimethylpyridin-3-yl)methanamine dihydrochloride (28.69 mg, 0.12 mmol) and N,N-diisopropylethylamine (34.84 L, 0.2 mmol). The reaction mixture was heated in a sealed vial at 100° C. for 30 min under microwave irradiation. The solvent was removed under reduced pressure and the residue was purified by flash chromatography (5% MeOH/DCM) to obtain the compound 9 as a white solid (32 mg, 75%). $^1$H NMR (500 MHz, Chloroform-d) δ 10.55 (s, 1H), 7.70 (dd, J=8.6, 2.3 Hz, 1H), 7.18 (d, J=7.4 Hz, 1H), 6.57 (s, 1H), 5.22 (s, 1H), 4.67-4.55 (m, 2H), 4.00 (s, 3H), 3.21-3.07 (m, 1H), 2.85 (dd, J=16.9, 3.8 Hz, 1H), 2.39 (s, 3H), 2.38 (s, 3H), 2.10-2.01 (m, 1H), 2.00-1.90 (m, 1H), 1.25 (d, J=6.6 Hz, 3H). $^{13}$C NMR (126 MHz, CDCl$_3$) δ 170.97 (d, J=2.52 Hz), 170.63, 162.35, 161.35, 157.42 (d, J=243.18 Hz), 154.88, 148.38, 132.55, 126.81 (d, J=23.94 Hz), 120.98 (d, J=23.94 Hz), 118.53, 117.60 (d, J=8.82 Hz), 115.01, 108.54 (d, J=22.68 Hz), 97.58, 53.65, 45.49, 34.36, 25.83, 23.97, 23.03, 18.97, 18.08. MS (ESI-TOF) for $C_{23}H_{24}FN_3O_4[M+H]^+$ calculated 426.1824; found, 426.1899.

9-Fluoro-N-((5-fluoropyridin-3-yl)methyl)-7-hydroxy-3-methyl-5-oxo-2,3-dihydro-1H,5H-pyrido[3,2,1-ij]quinoline-6-carboxamide (10)

(5-Fluoropyridin-3-yl)methanamine (15.14 mg, 0.12 mmol) was used as reagent. White solid (30 mg, 78%). $^1$H NMR (500 MHz, Chloroform-d) δ 16.46 (s, 1H), 10.94 (t, J=5.4 Hz, 1H), 8.45 (s, 1H), 8.40 (d, J=2.7 Hz, 1H), 7.75-7.70 (m, 1H), 7.48-7.43 (m, 1H), 7.25-7.21 (m, 1H), 5.28-5.19 (m, 1H), 4.76-4.60 (m, 2H), 3.25-3.11 (m, 1H), 2.94-2.82 (m, 1H), 2.13-2.06 (m, 1H), 2.03-1.94 (m, 1H), 1.29 (d, J=6.7 Hz, 3H). $^{13}$C NMR (126 MHz, CDCl$_3$) δ 171.45, 170.94 (d, J=2.52 Hz), 161.48, 159.69 (d, J=58.30 Hz), 157.53 (d, J=244.44 Hz), 145.10 (d, J=3.78 Hz), 137.45 (d, J=23.94 Hz), 135.57 (d, J=3.78 Hz), 132.59 (d, J=1.26 Hz), 127.10 (d, J=7.56 Hz), 122.38 (d, J=17.64 Hz), 121.49 (d, J=23.94 Hz), 117.31 (d, J=8.82 Hz), 108.63 (d, J=23.94 Hz), 97.40, 45.86, 40.00, 25.80, 22.99, 18.09. MS (ESI-TOF) for $C_{20}H_{17}F_2N_3O_3[M+H]^+$ calculated 386.1311; found, 386.1347.

N-((6-Chloropyridin-3-yl)methyl)-9-fluoro-7-hydroxy-3-methyl-5-oxo-2,3-dihydro-1H,5H-pyrido[3,2,1-ij]quinoline-6-carboxamide (11)

(6-Chloropyridin-3-yl)methanamine (17.11 mg, 0.12 mmol) was used as reagent. Yellow solid (32 mg, 80%). $^1$H NMR (500 MHz, Chloroform-d) δ 16.48 (s, 1H), 10.90 (s, 1H), 8.41 (d, J=2.1 Hz, 1H), 7.75-7.65 (m, 2H), 7.31 (d, J=8.2 Hz, 1H), 7.25-7.20 (m, 1H), 5.27-5.18 (m, 1H), 4.69-4.56 (m, 2H), 3.24-3.09 (m, 1H), 2.94-2.83 (m, 1H), 2.13-2.05 (m, 1H), 2.03-1.92 (m, 1H), 1.28 (d, J=6.7 Hz, 3H). $^{13}$C NMR (126 MHz, CDCl$_3$) δ 171.38, 170.93 (d, J=2.52 Hz), 161.47, 157.53 (d, J=243.18 Hz), 150.76, 149.30, 138.63, 132.76, 132.58, 127.09 (d, J=6.30 Hz), 124.46, 121.48 (d, J=23.94 Hz), 117.32 (d, J=8.82 Hz), 108.62 (d, J=23.94 Hz), 97.40, 45.84, 39.92, 25.81, 22.98, 18.08. MS (ESI-TOF) for $C_{20}H_{17}C_1FN_3O_3[M+H]^+$ calculated 402.1015; found, 402.1014.

9-Fluoro-7-hydroxy-3-methyl-5-oxo-N-((6-(trifluoromethyl)pyridin-3-yl)methyl)-2,3-dihydro-1H,5H-pyrido[3,2,1-ij]quinoline-6-carboxamide (12)

(6-(Trifluoromethyl)pyridin-3-yl)methanamine (21.14 mg, 0.12 mmol) was used as reagent. White solid (30 mg, 69%). $^1$H NMR (500 MHz, Chloroform-d) δ 16.38 (s, 1H), 11.00 (t, J=5.6 Hz, 1H), 8.75 (d, J=1.8 Hz, 1H), 7.93-7.88 (m, 1H), 7.74-7.70 (m, 1H), 7.67 (d, J=7.9 Hz, 1H), 7.25-7.22 (m, 1H), 5.28-5.19 (m, 1H), 4.79-4.66 (m, 2H), 3.23-3.12 (m, 1H), 2.93-2.85 (m, 1H), 2.14-2.06 (m, 1H), 2.04-1.94 (m, 1H), 1.29 (d, J=6.7 Hz, 3H). $^{13}$C NMR (126 MHz, CDCl$_3$) δ 171.52, 170.92 (d, J=3.78 Hz), 161.49, 157.54 (d, J=243.18 Hz), 149.63, 147.48 (q, J=34.80 Hz), 37.10, 136.84, 132.60, 127.13 (d, J=7.56 Hz), 122.72, 121.55 (d, J=23.94 Hz), 120.57 (q, J=2.60 Hz), 117.28 (d, J=7.56 Hz), 108.64 (d, J=23.94 Hz), 97.39, 45.88, 40.30, 25.80, 22.98, 18.08. MS (ESI-TOF) for $C_{21}H_{17}F_4N_3O_3[M+H]^+$ calculated 436.1279; found, 436.1386.

Methyl 5-((9-fluoro-7-hydroxy-3-methyl-5-oxo-2,3-dihydro-1H,5H-pyrido[3,2,1-ij]quinoline-6-carboxamido)methyl)picolinate (13)

Methyl 5-(aminomethyl)pyridine-2-carboxylate dihydrochloride (28.69 mg, 0.12 mmol) was used as reagent. White solid (26 mg, 61%). $^1$H NMR (500 MHz, Chloroform-d) δ 16.43 (s, 1H), 10.98 (t, J=5.8 Hz, 1H), 8.75 (d, J=1.7 Hz, 1H), 8.12 (d, J=8.1 Hz, 1H), 7.87 (dd, J=8.1, 2.2 Hz, 1H), 7.75-7.69 (m, 1H), 7.25-7.20 (m, 1H), 5.28-5.18 (m, 1H), 4.80-4.66 (m, 2H), 4.00 (s, 3H), 3.24-3.11 (m, 1H), 2.94-2.84 (m, 1H), 2.13-2.06 (m, 1H), 2.03-1.93 (m, 1H), 1.29 (d, J=6.7 Hz, 3H). $^{13}$C NMR (126 MHz, CDCl$_3$) δ 171.48, 170.92 (d, J=2.52 Hz), 165.67, 161.48, 157.53 (d, J=244.44 Hz), 149.41, 147.15, 137.63, 136.43, 132.59, 127.10 (d, J=7.56 Hz), 125.31, 121.50 (d, J=23.94 Hz), 117.30 (d, J=8.82 Hz), 108.63 (d, J=23.94 Hz), 97.41, 53.08, 45.86, 40.42, 25.80, 22.98, MS (ESI-TOF) for C$_{22}$H$_{20}$FN$_3$O$_5$[M+H]$^+$ calculated 426.1460; found, 426.1508.

N-((6-Aminopyridin-3-yl)methyl)-9-fluoro-7-hydroxy-3-methyl-5-oxo-2,3-dihydro-1H,5H-pyrido[3,2,1-ij]quinoline-6-carboxamide (14)

5-(Aminomethyl)pyridin-2-amine (14.78 mg, 0.12 mmol) was used as reagent. Pale yellow solid (31 mg, 81%). $^1$H NMR (500 MHz, Chloroform-d) δ 10.67 (s, 1H), 8.08 (s, 1H), 7.78-7.65 (m, 1H), 7.55-7.41 (m, 1H), 7.23-7.18 (m, 1H), 6.49 (d, J=8.4 Hz, 1H), 5.27-5.15 (m, 1H), 4.56-4.34 (m, 4H), 3.23-3.06 (m, 1H), 2.87 (dd, J=16.9, 3.6 Hz, 1H), 2.11-1.90 (m, 2H), 1.27 (d, J=6.6 Hz, 3H). $^{13}$C NMR (126 MHz, CDCl$_3$) δ 171.00, 170.98, 161.47, 158.03, 157.49 (d, J=243.18 Hz), 147.96, 138.19, 132.55, 126.97 (d, J=7.56 Hz), 123.53, 121.21 (d, J=23.94 Hz), 117.51 (d, J=8.82 Hz), 108.59 (d, J=23.94 Hz), 108.50, 97.48, 45.72, 40.39, 25.83, 23.01, 18.08. MS (ESI-TOF) for C$_{20}$H$_{19}$FN$_4$O$_3$[M+H]$^+$ calculated 383.1514; found, 383.1614.

N-((6-(Dimethylamino)pyridin-3-yl)methyl)-9-fluoro-7-hydroxy-3-methyl-5-oxo-2,3-dihydro-1H,5H-pyrido[3,2,1-ij]quinoline-6-carboxamide (15)

5-(Aminomethyl)-N,N-dimethylpyridin-2-amine (18.14 mg, 0.12 mmol) was used as reagent. Yellow solid (28 mg, 68%). $^1$H NMR (500 MHz, Chloroform-d) δ 16.94 (s, 1H), 10.63 (s, 1H), 8.17 (d, J=2.1 Hz, 1H), 7.74-7.68 (m, 1H), 7.50 (dd, J=8.8, 2.5 Hz, 1H), 7.23-7.17 (m, 1H), 6.53-6.47 (m, 1H), 5.25-5.16 (m, 1H), 4.55-4.43 (m, 2H), 3.23-3.11 (m, 1H), 3.07 (s, 6H), 2.90-2.81 (m, 1H), 2.11-2.02 (m, 1H), 2.01-1.91 (m, 1H), 1.26 (d, J=6.7 Hz, 3H). $^{13}$C NMR (126 MHz, CDCl$_3$) δ 170.97 (d, J=2.52 Hz), 170.88, 161.42, 159.08, 157.45 (d, J=243.18 Hz), 147.72, 137.57, 132.52, 126.93 (d, J=7.56 Hz), 121.14 (d, J=23.94 Hz), 120.54, 117.51 (d, J=8.82 Hz), 108.56 (d, J=23.94 Hz), 106.00, 97.47, 45.66, 40.48, 38.34, 25.81, 23.00, 18.07. MS (ESI-TOF) for C$_{22}$H$_{23}$FN$_4$O$_3$[M+H]$^+$ calculated 411.1827; found, 411.1842.

N-((2-(Dimethylamino)pyridin-3-yl)methyl)-9-fluoro-7-hydroxy-3-methyl-5-oxo-2,3-dihydro-1H,5H-pyrido[3,2,1-ij]quinoline-6-carboxamide (16)

3-(Aminomethyl)-N,N-dimethylpyridin-2-amine (18.14 mg, 0.12 mmol) was used as reagent. Pale yellow solid (35 mg, 85%). $^1$H NMR (500 MHz, Chloroform-d) δ 16.79 (s, 1H), 10.85 (t, J=5.4 Hz, 1H), 8.21 (dd, J=4.8, 1.9 Hz, 1H), 7.75-7.70 (m, 1H), 7.64-7.58 (m, 1H), 7.24-7.19 (m, 1H), 6.93-6.87 (m, 1H), 5.28-5.20 (m, 1H), 4.76-4.61 (m, 2H), 3.24-3.11 (m, 1H), 2.93-2.84 (m, 7H), 2.12-2.04 (m, 1H), 2.03-1.92 (m, 1H), 1.28 (d, J=6.6 Hz, 3H). $^{13}$C NMR (126 MHz, CDCl$_3$) δ 171.28, 170.93 (d, J=3.78 Hz), 162.05, 161.48, 157.48 (d, J=244.44 Hz), 146.54, 137.23, 132.58, 126.98 (d, J=7.56 Hz), 124.07, 121.27 (d, J=23.94 Hz), 117.67, 117.45 (d, J=8.82 Hz), 108.59 (d, J=23.94 Hz), 97.49, 45.70, 42.53, 39.33, 25.82, 23.01, 18.09. MS (ESI-TOF) for C$_{22}$H$_{23}$FN$_4$O$_3$[M+H]$^+$ calculated 411.1827; found, 411.1939.

9-Fluoro-7-hydroxy-3-methyl-5-oxo-N-((6-(pyrrolidin-1-yl)pyridin-3-yl)methyl)-2,3-dihydro-1H,5H-pyrido[3,2,1-ij]quinoline-6-carboxamide (17)

(6-(Pyrrolidin-1-yl)pyridin-3-yl)methanamine (22.27 mg, 0.12 mmol) was used as reagent. White solid (24 mg, 55%). $^1$H NMR (500 MHz, Chloroform-d) δ 16.96 (s, 1H), 10.61 (t, J=5.0 Hz, 1H), 8.15 (d, J=2.1 Hz, 1H), 7.74-7.68 (m, 1H), 7.49 (dd, J=8.7, 2.4 Hz, 1H), 7.20 (dd, J=8.3, 2.5 Hz, 1H), 6.35 (d, J=8.6 Hz, 1H), 5.25-5.16 (m, 1H), 4.54-4.43 (m, 2H), 3.44 (t, J=6.6 Hz, 4H), 3.23-3.08 (m, 1H), 2.92-2.81 (m, 1H), 2.12-1.90 (m, 6H), 1.26 (d, J=6.7 Hz, 3H). $^{13}$C NMR (126 MHz, CDCl$_3$) δ 170.98 (d, J=2.52 Hz), 170.86, 161.42, 157.45 (d, J=243.18 Hz), 157.00, 148.01, 137.48, 132.53, 126.92 (d, J=7.56 Hz), 121.13 (d, J=23.94 Hz), 120.14, 117.53 (d, J=8.82 Hz), 108.57 (d, J=23.94 Hz), 106.72, 97.48, 46.89, 45.66, 40.61, 25.82, 25.69, 23.01, 18.08. MS (ESI-TOF) for C$_{24}$H$_{25}$FN$_4$O$_3$[M+H]$^+$ calculated 437.1983; found, 437.2031.

N-((6-(1H-Imidazol-1-yl)pyridin-3-yl)methyl)-9-fluoro-7-hydroxy-3-methyl-5-oxo-2,3-dihydro-1H,5H-pyrido[3,2,1-ij]quinoline-6-carboxamide (18)

(6-(1H-Imidazol-1-yl)pyridin-3-yl)methanamine (20.9 mg, 0.12 mmol) was used as reagent. White solid (33 mg, 76%). $^1$H NMR (500 MHz, Chloroform-d) δ 16.51 (s, 1H), 10.94 (t, J=5.6 Hz, 1H), 8.50 (d, J=1.8 Hz, 1H), 8.35-8.30 (m, 1H), 7.87 (dd, J=8.4, 2.4 Hz, 1H), 7.75-7.69 (m, 1H), 7.63 (t, J=1.3 Hz, 1H), 7.36-7.32 (m, 1H), 7.25-7.22 (m, 1H), 7.20-7.18 (m, 1H), 5.27-5.19 (m, 1H), 4.74-4.60 (m, 2H), 3.24-3.10 (m, 1H), 2.94-2.84 (m, 1H), 2.15-2.05 (m, 1H), 2.04-1.92 (m, 1H), 1.29 (d, J=6.7 Hz, 3H). $^{13}$C NMR (126 MHz, CDCl$_3$) δ 171.39, 170.94 (d, J=2.52 Hz), 161.49, 157.53 (d, J=243.18 Hz), 148.74, 148.57, 138.89, 135.11, 132.56, 132.30, 130.85, 127.10 (d, J=7.56 Hz), 121.49 (d, J=23.94 Hz), 117.33 (d, J=7.56 Hz), 116.31, 112.38, 108.62 (d, J=23.94 Hz), 97.42, 45.85, 40.11, 25.80, 22.98, 18.08. MS (ESI-TOF) for C$_{23}$H$_{20}$FN$_5$O$_3$ [M+H]$^+$ calculated 434.1623; found, 434.1658.

9-Fluoro-7-hydroxy-3-methyl-5-oxo-N-(pyridin-2-ylmethyl)-2,3-dihydro-1H,5H-pyrido[3,2,1-ij]quinoline-6-carboxamide (19)

2-(Aminomethyl)pyridine (12.37 μL, 0.12 mmol) was used as reagent. White solid (30 mg, 82%). $^1$H NMR (500 MHz, DMSO-d$_6$) δ 11.05 (t, J=5.4 Hz, 1H), 8.63-8.53 (m, 1H), 7.83-7.77 (m, 1H), 7.66-7.55 (m, 2H), 7.41 (d, J=7.8 Hz, 1H), 7.35-7.30 (m, 1H), 5.18-5.09 (m, 1H), 4.80-4.66 (m, 2H), 3.18-3.06 (m, 1H), 2.98-2.89 (m, 1H), 2.12-2.03 (m, 1H), 1.96-1.84 (m, 1H), 1.22 (d, J=6.6 Hz, 3H). $^{13}$C NMR (126 MHz, DMSO-d$_6$) δ 170.52, 170.20 (d, J=3.78 Hz), 160.32, 156.69 (d, J=240.66 Hz), 156.38, 149.13, 137.00, 132.55, 128.14 (d, J=8.82 Hz), 122.54, 121.63, 121.46 (d, J=23.94 Hz), 116.13 (d, J=8.82 Hz), 107.15 (d, J=22.68 Hz), 96.67, 45.42, 44.08, 24.85, 22.13, 17.68. MS (ESI-TOF) for C$_{20}$H$_{18}$FN$_3$O$_3$[M+H]$^+$ calculated 368.1405; found, 368.1448.

9-Fluoro-7-hydroxy-3-methyl-5-oxo-N-(pyridin-4-ylmethyl)-2,3-dihydro-1H,5H-pyrido[3,2,1-ij]quinoline-6-carboxamide (20)

4-(Aminomethyl)pyridine (12.18 μL, 0.12 mmol) was used as reagent. White solid (29 mg, 79%). $^1$H NMR (500

MHz, DMSO-$d_6$) δ 10.88 (t, J=6.1 Hz, 1H), 8.56-8.48 (m, 2H), 7.67-7.55 (m, 2H), 7.38-7.27 (m, 2H), 5.18-5.06 (m, 1H), 4.71-4.58 (m, 2H), 3.17-3.07 (m, 1H), 2.98-2.90 (m, 1H), 2.12-2.04 (m, 1H), 1.96-1.84 (m, 1H), 1.23 (d, J=6.6 Hz, 3H). $^{13}$C NMR (126 MHz, DMSO-$d_6$) δ 170.86, 170.13 (d, J=2.52 Hz), 160.33, 156.71 (d, J=241.92 Hz), 149.74, 147.30, 132.55, 128.19 (d, J=7.56 Hz), 122.24, 121.55 (d, J=23.94 Hz), 116.05 (d, J=8.82 Hz), 107.15 (d, J=23.94 Hz), 96.66, 45.52, 41.38, 24.85, 22.11, 17.64. MS (ESI-TOF) for $C_{20}H_{18}FN_3O_3[M+H]^+$ calculated 368.1405; found, 368.1539.

9-Fluoro-7-hydroxy-N-((2-methoxypyridin-4-yl)methyl)-3-methyl-5-oxo-2,3-dihydro-1H,5H-pyrido[3,2,1-ij]quinoline-6-carboxamide (21)

(2-Methoxypyridin-4-yl)methanamine (16.58 mg, 0.12 mmol) was used as reagent. Yellow solid (25 mg, 63%). $^1$H NMR (500 MHz, Chloroform-d) δ 16.56 (s, 1H), 10.90 (t, J=5.5 Hz, 1H), 8.12 (dd, J=5.3, 0.5 Hz, 1H), 7.75-7.68 (m, 1H), 7.25-7.20 (m, 1H), 6.89-6.84 (m, 1H), 6.72 (dd, J=1.4, 0.7 Hz, 1H), 5.30-5.19 (m, 1H), 4.69-4.51 (m, 2H), 3.92 (s, 3H), 3.24-3.10 (m, 1H), 2.89 (dd, J=16.9, 3.9 Hz, 1H), 2.13-2.06 (m, 1H), 2.04-1.94 (m, 1H), 1.30 (d, J=6.7 Hz, 3H). $^{13}$C NMR (126 MHz, CDCl$_3$) δ 171.42, 170.95 (d, J=2.52 Hz), 164.79, 161.52, 157.52 (d, J=244.44 Hz), 149,83, 147.30, 132.60, 127.06 (d, J=7.56 Hz), 121.41 (d, J=23.94 Hz), 117.37 (d, J=8.82 Hz), 115.77, 109.15, 108.63 (d, J=23.94 Hz), 97.43, 53.62, 45.81, 41.90, 25.82, 23.00, 18.10. MS (ESI-TOF) for $C_{21}H_{20}FN_3O_4[M+H]^+$ calculated 398.1511; found, 398.1560.

9-Fluoro-7-hydroxy-3-methyl-5-oxo-N-(pyridazin-4-ylmethyl)-2,3-dihydro-1H,5H-pyrido[3,2,1-ij]quinoline-6-carboxamide (22)

Pyridazin-4-ylmethanamine (13.09 mg, 0.12 mmol) was used as reagent. Red solid (28 mg, 76%). $^1$H NMR (500 MHz, Chloroform-d) δ 16.20 (s, 1H), 11.06 (t, J=5.5 Hz, 1H), 9.24-9.22 (m, 1H), 9.15 (dd, J=5.3, 1.1 Hz, 1H), 7.74-7.70 (m, 1H), 7.49-7.46 (m, 1H), 7.26-7.23 (m, 1H), 5.30-5.21 (m, 1H), 4.78-4.58 (m, 2H), 3.24-3.12 (m, 1H), 2.93-2.85 (m, 1H), 2.15-2.06 (m, 1H), 2.05-1.94 (m, 1H), 1.30 (d, J=6.7 Hz, 3H). $^{13}$C NMR (126 MHz, CDCl$_3$) δ 171.77, 170.93 (d, J=2.52 Hz), 161.50, 157.57 (d, J=244.44 Hz), 151.40, 151.27, 137.87, 132.65, 127.19 (d, J=7.56 Hz), 124.86, 121.67 (d, J=23.94 Hz), 117.21 (d, J=8.82 Hz), 108.67 (d, J=23.94 Hz), 97.34, 45.94, 39.93, 25.80, 22.98, MS (ESI-TOF) for $C_{19}H_{17}FN_4O_3[M+H]^+$ calculated 369.1357; found, 369.1397.

9-Fluoro-7-hydroxy-3-methyl-5-oxo-N-(pyrimidin-5-ylmethyl)-2,3-dihydro-1H,5H-pyrido[3,2,1-ij]quinoline-6-carboxamide (23)

Pyrimidin-5-ylmethanamine (13.09 mg, 0.12 mmol) was used as reagent. Pale yellow solid (27 mg, 73%). $^1$H NMR (500 MHz, Chloroform-d) δ 16.35 (s, 1H), 10.98 (t, J=5.1 Hz, 1H), 9.16 (s, 1H), 8.79 (s, 2H), 7.72 (dd, J=8.6, 2.6 Hz, 1H), 7.23 (dd, J=8.2, 2.8 Hz, 1H), 5.28-5.18 (m, 1H), 4.70-4.59 (m, 2H), 3.24-3.12 (m, 1H), 2.92-2.84 (m, 1H), 2.13-2.06 (m, 1H), 2.04-1.93 (m, 1H), 1.29 (d, J=6.7 Hz, 3H). $^{13}$CNMR (126 MHz, CDCl$_3$) δ 171.55, 170.91 (d, J=2.52 Hz), 161.46, 158.11, 157.54 (d, J=244.44 Hz), 156.68, 132.60, 132.59, 131.76, 127.12 (d, J=7.56 Hz), 121.55 (d, J=23.94 Hz),117.26 (d, J=8.82 Hz), 108.64 (d, J=23.94 Hz), 97.39, 45.88, 38.49, 25.80, 22.98, 18.08. MS (ESI-TOF) for $C_{19}H_{17}FN_4O_3[M+H]^+$ calculated 369.1357; found, 369.1360.

9-Fluoro-7-hydroxy-3-methyl-5-oxo-N-(pyridazin-3-ylmethyl)-2,3-dihydro-1H,5H-pyrido[3,2,1-ij]quinoline-6-carboxamide (24)

Pyridazin-3-ylmethanamine (13.09 mg, 0.12 mmol) was used as reagent. White solid (28 mg, 76%). $^1$H NMR (500 MHz, Chloroform-d) δ 16.46 (s, 1H), 11.14 (t, J=5.4 Hz, 1H), 9.14 (dd, J=4.9, 1.6 Hz, 1H), 7.74-7.70 (m, 1H), 7.60 (dd, J=8.5, 1.6 Hz, 1H), 7.49-7.45 (m, 1H), 7.25-7.21 (m, 1H), 5.29-5.23 (m, 1H), 5.08-4.94 (m, 2H), 3.23-3.11 (m, 1H), 2.92-2.85 (m, 1H), 2.13-2.05 (m, 1H), 2.03-1.92 (m, 1H), 1.29 (d, J=6.7 Hz, 3H). $^{13}$C NMR (126 MHz, CDCl$_3$) δ 171.69, 170.87 (d, J=2.52 Hz), 161.43, 160.02, 157.50 (d, J=244.44 Hz), 150.74, 132.67, 127.09 (d, J=7.56 Hz), 127.03, 125.72, 121.45 (d, J=23.94 Hz), 117.26 (d, J=8.82 Hz), 108.60 (d, J=22.68 Hz), 97.53, 45.80, 43.37, 25.81, 23.01, 18.09. MS (ESI-TOF) for $C_{19}H_{17}FN_4O_3[M+H]^+$ calculated 369.1357; found, 369.1378.

9-Fluoro-7-hydroxy-3-methyl-5-oxo-N-(pyridin-3-yl)-2,3-dihydro-1H,5H-pyrido[3,2,1-ij]quinoline-6-carboxamide (25)

3-Aminopyridine (11.29 mg, 0.12 mmol) was used as reagent. White solid (26 mg, 74.0%). $^1$H NMR (500 MHz, DMSO-$d_6$) δ 16.22 (s, 1H), 12.80 (s, 1H), 8.85 (d, J=2.4 Hz, 1H), 8.43-8.37 (m, 1H), 8.18-8.13 (m, 1H), 7.71-7.60 (m, 2H), 7.50-7.43 (m, 1H), 5.22-5.15 (m, 1H), 3.21-3.09 (m, 1H), 3.01-2.92 (m, 1H), 2.16-2.07 (m, 1H), 2.00-1.89 (m, 1H), 1.27 (d, J=6.6 Hz, 3H). $^{13}$C NMR (126 MHz, DMSO-$d_6$) δ 170.22 (d, J=2.52 Hz), 169.44, 160.63, 156.90 (d, J=241.92 Hz), 145.89, 142.46, 133.51, 132.54, 128.51 (d, J=7.56 Hz), 128.34, 123.99, 122.05 (d, J=23.94 Hz), 115.94 (d, J=7.56 Hz), 107.24 (d, J=23.94 Hz), 97.06, 45.93, 24.81, 22.06, 17.63. MS (ESI-TOF) for $C_{19}H_{16}FN_3O_3[M+H]^+$ calculated 354.1248; found, 354.1266.

9-Fluoro-7-hydroxy-3-methyl-5-oxo-N-(2-(pyridin-3-yl)ethyl)-2,3-dihydro-1H,5H-pyrido[3,2,1-ij]quinoline-6-carboxamide (26)

3-(2-Aminoethyl)pyridine (14.66 mg, 0.12 mmol) was used as reagent. White solid (27 mg, 71%). $^1$H NMR (500 MHz, DMSO-$d_6$) δ 10.49 (t, J=5.8 Hz, 1H), 8.49 (d, J=1.7 Hz, 1H), 8.43 (dd, J=4.8, 1.6 Hz, 1H), 7.73-7.69 (m, 1H), 7.64-7.54 (m, 2H), 7.36-7.31 (m, 1H), 5.17-5.02 (m, 1H), 3.74-3.57 (m, 2H), 3.18-3.04 (m, 1H), 2.97-2.88 (m, 3H), 2.12-2.02 (m, 1H), 1.95-1.84 (m, 1H), 1.20 (d, J=6.6 Hz, 3H).$^{13}$C NMR (126 MHz, DMSO-$d_6$) δ 170.52, 170.23 (d, J=3.78 Hz), 160.31, 156.69 (d, J=240.66 Hz), 149.91, 147.69, 136.28, 134.45, 132.45, 128.15 (d, J=7.56 Hz), 123.55, 121.42 (d, J=23.94 Hz), 116.17 (d, J=8.82 Hz), 107.12 (d, J=23.94 Hz), 96.40, 45.41, 31.89, 24.81, 22.10, 17.63. MS (ESI-TOF) for $C_{21}H_{20}FN_3O_3[M+H]^+$ calculated 382.1561; found, 382.1649.

N-(6,7-Dihydro-5H-cyclopenta[b]pyridin-5-yl)-9-fluoro-7-hydroxy-3-methyl-5-oxo-2,3-dihydro-1H,5H-pyrido[3,2,1-ij]quinoline-6-carboxamide (27)

6,7-Dihydro-5H-cyclopenta[b]pyridin-5-amine dihydrochloride (24.85 mg, 0.12 mmol) was used as reagent. White solid (22 mg, 56%). 1H NMR (500 MHz, Chloroform-d) δ

10.78 (d, J=7.0 Hz, 1H), 8.46 (s, 1H), 7.78-7.64 (m, 2H), 7.23 (d, J=8.5 Hz, 1H), 7.16-7.08 (m, 1H), 5.67 (q, J=7.6 Hz, 1H), 5.26-5.14 (m, 1H), 3.22-2.98 (m, 3H), 2.93-2.65 (m, 2H), 2.19-1.88 (m, 3H), 1.27 (d, J=6.5 Hz, 3H). $^{13}$C NMR (126 MHz, CDCl$_3$) δ 171.09, 164.34, 164.28, 161.50 (d, J=2.52 Hz), 157.54 (d, J=243.18 Hz), 149.61, 136.40, 132.85, 132.67, 127.04 (d, J=7.56 Hz), 121.90, 121.35 (d, J=23.94 Hz), 117.50 (d, J=10.08 Hz), 108.62 (d, J=23.94 Hz), 97.40, 52.66, 45.74, 32.42, 32.00, 31.91, 25.82, 18.09. MS (ESI-TOF) for C$_{22}$H$_{20}$FN$_3$O$_3$[M+H]$^+$ calculated 394.1561; found, 394.1588.

N-((1H-Indol-2-yl)methyl)-9-fluoro-7-hydroxy-3-methyl-5-oxo-2,3-dihydro-1H,5H-pyrido[3,2,1-ij]quinoline-6-carboxamide (28)

(1H-Indol-2-yl)methanamine (17.54 mg, 0.12 mmol) was used as reagent. White solid (25 mg, 62%). $^1$H NMR (500 MHz, Chloroform-d) δ 16.49 (s, 1H), 10.95 (t, J=5.6 Hz, 1H), 8.89 (s, 1H), 7.75-7.68 (m, 1H), 7.58-7.54 (m, 1H), 7.37-7.33 (m, 1H), 7.24-7.20 (m, 1H), 7.18-7.12 (m, 1H), 7.10-7.04 (m, 1H), 6.44-6.39 (m, 1H), 5.26-5.17 (m, 1H), 4.77-4.64 (m, 2H), 3.25-3.08 (m, 1H), 2.96-2.79 (m, 1H), 2.14-2.03 (m, 1H), 2.02-1.91 (m, 1H), 1.26 (d, J=6.7 Hz, 3H). $^{13}$C NMR (126 MHz, CDCl$_3$) δ 172.04, 170.73 (d, J=3.78 Hz), 161.30, 157.50 (d, J=243.18 Hz), 136.47, 135.77, 132.61, 127.91, 127.09 (d, J=7.56 Hz), 122.17, 121.44 (d, J=23.94 Hz), 120.57, 119.87, 117.22 (d, J=8.82 Hz), 111.10, 108.56 (d, J=23.94 Hz), 101.39, 97.57, 45.82, 36.99, 25.79, 22.99, 18.05. MS (ESI-TOF) for C$_{23}$H$_{20}$FN$_3$O$_3$[M+H]$^+$ calculated 406.1561; found, 406.1548.

N-((1H-Indol-4-yl)methyl)-9-fluoro-7-hydroxy-3-methyl-5-oxo-2,3-dihydro-1H,5H-pyrido[3,2,1-ij]quinoline-6-carboxamide (29)

(1H-Indol-4-yl)methanamine (17.54 mg, 0.12 mmol) was used as reagent. Yellow solid (35 mg, 86%). $^1$H NMR (500 MHz, Chloroform-d) δ 17.10 (s, 1H), 10.80 (s, 1H), 8.27 (s, 1H), 7.77-7.68 (m, 1H), 7.35 (d, J=8.0 Hz, 1H), 7.25-7.12 (m, 4H), 6.82-6.61 (m, 1H), 5.27-5.15 (m, 1H), 5.05-4.82 (m, 2H), 3.22-3.05 (m, 1H), 2.89-2.79 (m, 1H), 2.09-2.00 (m, 1H), 1.99-1.90 (m, 1H), 1.25 (d, J=6.6 Hz, 3H). $^{13}$CNMR (126 MHz, CDCl$_3$) δ 171.04 (d, J=2.52 Hz), 170.85, 161.48, 157.45 (d, J=243.18 Hz), 136.04, 132.54, 129.31, 126.89 (d, J=7.56 Hz), 126.73, 124.43, 122.28, 121.09 (d, J=23.94 Hz), 19.22, 117.59 (d, J=8.82 Hz), 110.81, 108.57 (d, J=23.94 Hz), 100.96, 97.56, 45.59, 41.49, 25.80, 23.00, 18.08. MS (ESI-TOF) for C$_{23}$H$_{20}$FN$_3$O$_3$[M+H]$^+$ calculated 406.1561; found, 406.1554.

N-((1H-Indol-5-yl)methyl)-9-fluoro-7-hydroxy-3-methyl-5-oxo-2,3-dihydro-1H,5H-pyrido[3,2,1-j]quinoline-6-carboxamide (30)

(1H-Indol-5-yl)methanamine (17.54 mg, 0.12 mmol) was used as reagent. Pale yellow solid (33 mg, 81%). $^1$H NMR (500 MHz, Chloroform-d) δ 10.74 (s, 1H), 8.18 (s, 1H), 7.75-7.69 (m, 1H), 7.65 (s, 1H), 7.37 (d, J=8.3 Hz, 1H), 7.24-7.16 (m, 3H), 6.53 (s, 1H), 5.27-5.17 (m, 1H), 4.83-4.65 (m, 2H), 3.22-3.09 (m, 1H), 2.86 (dd, J=16.8, 3.6 Hz, 1H), 2.14-1.87 (m, 2H), 1.26 (d, J=6.6 Hz, 3H). $^{13}$C NMR (126 MHz, CDCl$_3$) δ 171.07 (d, J=3.78 Hz), 170.75, 161.50, 157.46 (d, J=243.18 Hz), 135.40, 132.53, 129.23, 128.25, 126.88 (d, J=6.30 Hz), 124.81, 122.48, 121.06 (d, J=23.94 Hz), 120.32, 117.64 (d, J=8.82 Hz), 111.45, 108.58 (d, J=23.94 Hz), 102.86, 97.56, 45.62, 43.79, 25.84, 23.02, 18.09. MS (ESI-TOF) for C$_{23}$H$_{20}$FN$_3$O$_3$[M+H]$^+$ calculated 406.1561; found, 406.1556.

N-((1H-Indol-7-yl)methyl)-9-fluoro-7-hydroxy-3-methyl-5-oxo-2,3-dihydro-1H,5H-pyrido[3,2,1-ij]quinoline-6-carboxamide (31)

7-(Aminomethyl)indole oxalate (28.35 mg, 0.12 mmol) was used as reagent. White solid (26 mg, 64%). $^1$H NMR (500 MHz, DMSO-d$_6$) δ 17.29 (s, 1H), 11.30 (s, 1H), 10.84 (t, J=5.7 Hz, 1H), 7.63 (dd, J=8.7, 2.9 Hz, 1H), 7.57 (dd, J=8.8, 2.8 Hz, 1H), 7.50 (d, J=7.8 Hz, 1H), 7.42 (t, J=2.8 Hz, 1H), 7.09 (d, J=6.9 Hz, 1H), 7.02-6.95 (m, 1H), 6.49 (dd, J=3.1, 1.9 Hz, 1H), 5.17-5.02 (m, 1H), 4.93-4.72 (m, 2H), 3.18-3.00 (m, 1H), 2.99-2.85 (m, 1H), 2.10-1.99 (m, 1H), 1.93-1.78 (m, 1H), 1.18 (d, J=6.6 Hz, 3H). $^{13}$C NMR (126 MHz, DMSO-d$_6$) δ 170.48, 170.21 (d, J=3.78 Hz), 160.32, 156.70 (d, J=240.66 Hz), 134.15, 132.47, 128.15 (d, J=8.82 Hz), 128.00, 125.50, 121.44 (d, J=23.94 Hz), 120.69, 120.63, 119.61, 118.94, 116.17 (d, J=8.82 Hz), 107.13 (d, J=23.94 Hz), 101.63, 96.65, 45.44, 24.83, 22.09, 17.63. MS (ESI-TOF) for C$_{23}$H$_{20}$FN$_3$O$_3$[M+H]$^+$ calculated 406.1561; found, 406.1592.

N-((1H-Indazol-3-yl)methyl)-9-fluoro-7-hydroxy-3-methyl-5-oxo-2,3-dihydro-1H,5H-pyrido[3,2,1-ij]quinoline-6-carboxamide (32)

(1H-Indazol-3-yl)methanamine (17.66 mg, 0.12 mmol) was used as reagent. White solid (15 mg, 37%). $^1$H NMR (500 MHz, Chloroform-d) δ 16.87 (s, 1H), 11.05 (s, 1H), 9.96 (s, 1H), 7.86-7.82 (m, 1H), 7.75-7.71 (m, 1H), 7.49-7.45 (m, 1H), 7.43-7.37 (m, 1H), 7.24-7.15 (m, 2H), 5.29-5.24 (m, 1H), 5.13-4.96 (m, 2H), 3.22-3.09 (m, 1H), 2.91-2.81 (m, 1H), 2.09-2.03 (m, 1H), 2.00-1.91 (m, 1H), 1.27 (d, J=6.8 Hz, 3H). $^{13}$C NMR (126 MHz, CDCl$_3$) δ 171.06, 170.93 (d, J=: 3.78 Hz), 161.46, 15747 (d, J=243.18 Hz), 143.06, 141.43, 132.62, 127.30, 126.96 (d, J=7.56 Hz), 121.47, 121.21 (d, J=23.94 Hz), 121.16, 120.37, 117.46 (d, J=8.82 Hz), 109.91, 108.58 (d, J=23.94 Hz), 97.61, 45.65, 36.29, 25.81, 23.02, 18.11. MS (ESI-TOF) for C$_{22}$H$_{19}$FN$_4$O$_3$[M+H]$^+$ calculated 407.1514; found, 407.1516.

N-((1H-Benzo[d]imidazol-2-yl)methyl)-9-fluoro-7-hydroxy-3-methyl-5-oxo-2,3-dihydro-1H,5H-pyrido[3,2,1-ij]quinoline-6-carboxamide (33)

(1H-Benzo[d]imidazol-2yl)methanamine (17.66 mg, 0.12 mmol) was used as reagent. White solid (32 mg, 79%). $^1$H NMR (500 MHz, DMSO-d$_6$) δ 12.43 (s, 1H), 11.00 (t, J=5.2 Hz, 1H), 7.76-7.38 (m, 4H), 7.22-7.09 (m, 2H), 5.27-5.05 (m, 1H), 4.92-4.74 (m, 2H), 3.20-3.07 (m, 1H), 2.99-2.91 (m, 1H), 2.13-2.05 (m, 1H), 1.95-1.86 (m, 1H), 1.24 (d, J=6.6 Hz, 3H). $^{13}$C NMR (126 MHz, DMSO-d$_6$) δ 170.72, 170.00, 160.25, 156.69 (d, J=240.66 Hz), 150.87, 132.52, 128.15 (d, J=7.56 Hz), 121.71, 121.64, 121.54, 121.50 (d, J=23.94 Hz), 121.45, 116.00 (d, J=7.56 Hz), 115.99, 115.97, 107.13 (d, J=22.68 Hz), 96.83, 45.46, 37.31, 24.85, 22.09, 17.63. MS (ESI-TOF) for C$_{22}$H$_{19}$FN$_4$O$_3$[M+H]$^+$ calculated 407.1514; found, 407.1584.

9-Fluoro-7-hydroxy-3-methyl-N-((1-methyl-H-benzo[d]imidazol-2-yl)methyl)-5-oxo-2,3-dihydro-1H,5H-pyrido[3,2,1-ij]quinoline-6-carboxamide (34)

(1-Methyl-1H-benzo[d]imidazol-2-yl)methanamine hydrochloride (23.72 mg, 0.12 mmol) was used as reagent.

White solid (29 mg, 69%). $^1$H NMR (500 MHz, Chloroform-d) δ 16.44 (s, 1H), 11.13 (t, J=5.0 Hz, 1H), 7.80-7.77 (m, 1H), 7.71 (dd, J=8.6, 2.5 Hz, 1H), 7.35-7.26 (m, 3H), 7.22 (dd, J=8.3, 2.7 Hz, 1H), 5.32-5.22 (m, 1H), 5.04-4.84 (m, 2H), 3.85 (s, 3H), 3.23-3.09 (m, 1H), 2.90-2.81 (m, 1H), 2.11-2.03 (m, 1H), 2.00-1.91 (m, 1H), 1.28 (d, J=6.7 Hz, 3H). $^{13}$CNMR (126 MHz, CDCl$_3$) δ 171.01, 170.74 (d, J=3.78 Hz), 161.32, 157.46 (d, J=243.18 Hz), 150.31, 142.53, 136.24, 132.72, 127.07 (d, J=7.56 Hz), 122.95, 122.29, 121.40 (d, J=23.94 Hz), 120.14, 117.20 (d, J=8.82 Hz), 109.36, 108.55 (d, J=23.94 I-Hz), 97.55, 45.72, 36.29, 30.16, 25.79, 23.01, 18.09. MS (ESI-TOF) for C$_{23}$H$_{21}$FN$_4$O$_3$ [M+H]$^+$ calculated 421.1670; found, 421.1698.

N-((1H-Pyrrolo[2,3-b]pyridin-4-yl)methyl)-9-fluoro-7-hydroxy-3-methyl-5-oxo-2,3-dihydro-1H,5H-pyrido[3,2,1-ij]quinoline-6-carboxamide (35)

(1H-Pyrrolo[2,3-b]pyridin-4-yl)methanamine (17.66 mg, 0.12 mmol) was used as reagent. White solid (29 mg, 71%). $^1$H NMR (500 MHz, DMSO-d$_6$) δ 17.12 (s, 1H), 11.73 (s, 1H), 10.94 (t, J=6.0 Hz, 1H), 8.19 (d, J=4.8 Hz, 1H), 7.66-7.54 (m, 2H), 7.51-7.45 (m, 1H), 7.01 (d, J=4.9 Hz, 1H), 6.64-6.57 (m, 1H), 5.15-5.06 (m, 1H), 4.97-4.82 (m, 2H), 3.17-3.05 (m, 1H), 2.97-2.88 (m, 1H), 2.11-2.02 (m, 1H), 1.96-1.84 (m, 1H), 1.21 (d, J=6.6 Hz, 3H). $^{13}$C NMR (126 MHz, DMSO-d$_6$) δ 170.60, 170.19 (d, J=3.78 Hz), 160.40, 156.72 (d, J=240.66 Hz), 148.57, 142.77, 138.22, 132.52, 128.21 (d, d=7.56 Hz), 125.94, 121.53 (d, J=23.94 Hz), 117.99, 116.11 (d, J=7.56 Hz), 113.57, 107.15 (d, J=23.94 Hz), 98.17, 96.61, 45.50, 24.83, 22.11, 17.65. MS (ESI-TOF) for C$_{22}$H$_{19}$FN$_4$O$_3$[M+H]$^+$ calculated 407.1514; found, 407.1554.

9-Fluoro-7-hydroxy-3-methyl-5-oxo-N-(quinolin-3-ylmethyl)-2,3-dihydro-1H,5H-pyrido[3,2,1-ij]quinoline-6-carboxamide (36)

Quinolin-3-ylmethanamine dihydrochloride (27.73 mg, 0.12 mmol) was used as reagent. White solid (27 mg, 65%). $^1$H NMR (500 MHz, Chloroform-d) δ 16.64 (s, 1H), 10.98 (t, J=5.4 Hz, 1H), 8.95 (d, J=2.2 Hz, 1H), 8.17-8.13 (m, 1H), 8.10 (d, J=8.5 Hz, 1H), 7.82 (dd, J=8.2, 1.1 Hz, 1H), 7.76-7.67 (m, 2H), 7.58-7.52 (m, 1H), 7.25-7.19 (m, 1H), 5.28-5.18 (m, 1H), 4.91-4.78 (m, 2H), 3.22-3.10 (m, 1H), 2.91-2.84 (m, 1H), 2.13-2.05 (m, 1H), 2.03-1.93 (m, 1H), 1.28 (d, J=6.7 Hz, 3H). $^{13}$CNMR (126 MHz, CDCl$_3$) δ 171.34, 170.97 (d, J=2.52 Hz), 161.51, 157.51 (d, J=243.18 Hz), 150.91, 147.74, 134.68, 132.59, 130.88, 129.54, 129.42, 128.01, 127.87, 127.05 (d, J=7.56 Hz), 127.04, 121.39 (d, J=23.94 Hz), 117.40 (d, J=7.56 Hz), 108.62 (d, J=23.94 Hz), 97.50, 45.81, 40.91, 25.81, 22.99, 18.09. MS (ESI-TOF) for C$_{24}$H$_{20}$FN$_3$O$_3$[M+H]$^+$ calculated 418.1561; found, 418.1632.

9-Fluoro-7-hydroxy-3-methyl-5-oxo-N-(quinolin-5-ylmethyl)-2,3-dihydro-1H,5H-pyrido[3,2,1-ij]quinoline-6-carboxamide (37)

Quinolin-5-ylmethanamine (18.98 mg, 0.12 mmol) was used as reagent. White solid (22 mg, 53%). $^1$H NMR (500 MHz, DMSO-d$_6$) δ 17.08 (s, 1H), 10.90 (t, J=5.9 Hz, 1H), 8.97 (dd, J=4.2, 1.5 Hz, 1H), 8.71 (d, J=8.5 Hz, 1H), 8.01 (d, J=8.5 Hz, 1H), 7.81-7.75 (m, 1H), 7.70-7.54 (m, 4H), 5.22-4.98 (m, 3H), 3.15-3.04 (m, 1H), 2.97-2.85 (m, 1H), 2.12-1.98 (m, 1H), 1.93-1.78 (m, 1H), 1.17 (d, J=6.6 Hz, 3H). C NMR (126 MHz, DMSO-d$_6$) δ 170.39, 170.14 (d, J=3.78 Hz), 160.37, 156.72 (d, J=240.66 Hz), 150.20, 147.54, 134.55, 132.59, 132.49, 129.47, 128.57, 128.20 (d, J=8.82 Hz), 126.46, 125.98, 121.73, 121.55 (d, J=23.94 Hz), 116.08 (d, J=8.82 Hz), 107.14 (d, J=22.68 Hz), 96.63, 45.49, 24.80, 22.08, 17.61. MS (ESI-TOF) for C$_{24}$H$_{20}$FN$_3$O$_3$[M+H]$^+$ calculated 418.1561; found, 418.1586.

N-(Benzo[d][1,3]dioxol-5-ylmethyl)-9-fluoro-7-hydroxy-3-methyl-5-oxo-2,3dihydro-1H,5H-pyrido[3,2,1-ij]quinoline-6-carboxamide (38)

Benzo[d][1,3]dioxol-5-ylmethanamine (14.94 µL, 0.12 mmol) was used as reagent. White solid (28 mg, 68%). $^1$H NMR (500 MHz, DMSO-d$_6$) δ 10.73 (t, J=5.9 Hz, 1H), 7.71-7.45 (m, 2H), 6.96 (d, J=1.4 Hz, 1H), 6.92-6.83 (m, 2H), 6.00 (s, 2H), 5.20-4.98 (m, 1H), 4.56-4.41 (m, 2H), 3.18-3.03 (m, 1H), 2.98-2.86 (m, 1H), 2.12-2.00 (m, 1H), 1.95-1.82 (m, 1H), 1.20 (d, J=6.6 Hz, 3H). $^{13}$C NMR (126 MHz, DMSO-d$_6$) δ 170.24, 170.21 (d, J=2.52 Hz), 160.34, 156.70 (d, J=241.92 Hz), 147.41, 146.49, 132.47, 131.85, 128.16 (d, J=7.56 Hz), 121.44 (d, J=23.94 Hz), 121.13, 116.16 (d, J=8.82 Hz), 108.38, 108.28, 107.12 (d, J=23.94 Hz), 100.98, 96.55, 45.45, 42, 12, 24.83, 22.10, 17.62, MS (ESI-TOF) for C$_{22}$H$_{19}$FN$_2$O$_5$[M+H]$^+$ calculated 411.1351; found, 411.1359.

N-((2,3-Dihydrobenzo[b][1,4]dioxin-6-yl)methyl)-9-fluoro-7-hydroxy-3-methyl-5-oxo-2,3-dihydro-1H,5H-pyrido[3,2,1-ij]quinoline-6-carboxamide (39)

2,3-Dihydro-1,4-benzodioxin-6-ylmethylamine (19.82 mg, 0.12 mmol) was used as reagent. White solid (29 mg, 68%). $^1$H NMR (500 MHz, Chloroform-d) δ 16.92 (s, 1H), 10.70 (t, J=4.6 Hz, 1H), 7.75-7.69 (m, 1H), 7.23-7.18 (m, 1H), 6.91-6.80 (m, 3H), 5.27-5.18 (m, 1H), 4.62-4.44 (m, 2H), 4.24 (s, 4H), 3.23-3.10 (m, 1H), 2.87 (dd, J=16.9, 4.0 Hz, 1H), 2.11-2.03 (m, 1H), 2.02-1.91 (m, 1H), 1.28 (d, J=6.7 Hz, 3H). $^{13}$C NMR (126 MHz, CDCl$_3$) δ 171.00 (d, J=2.52 Hz), 170.91, 161.48, 157.46 (d, J=243.18 Hz), 143.70, 143.07, 132.53, 131.14, 126.93 (d, J=7.56 Hz), 121.17 (d, J=23.94 Hz), 120.96, 117.60, 117.53 (d, J=8.82 Hz), 116.87, 108.59 (d, J=23.94 Hz), 97.49, 64.49, 64.48, 45.67, 42.68, 25.83, 23.01, 18.09. MS (ESI-TOF) for C$_{23}$H$_{21}$FN$_2$O$_5$[M+H]$^+$ calculated 425.1507; found, 425.1490.

N-(3-Carbamoylbenzyl)-9-fluoro-7-hydroxy-3-methyl-5-oxo-2,3-dihydro-1H,5H-pyrido[3,2,1-ij]quinoline-6-carboxamide (40)

3-(Aminomethyl)benzamide (18.02 mg, 0.12 mmol) was used as reagent. White solid (33 mg, 81%). $^1$H NMR (500 MHz, DMSO-d$_6$) δ 10.83 (t, J=5.8 Hz, 1H), 7.99 (s, 1H), 7.87 (s, 1H), 7.79 (d, J=7.6 Hz, 1H), 7.65-7.49 (m, 3H), 7.44 (t, J=7.6 Hz, 1H), 7.37 (s, 1H), 5.17-5.03 (m, 1H), 4.75-4.53 (m, 2H), 3.17-3.05 (m, 1H), 3.00-2.86 (m, 1H), 2.11-2.00 (m, 1H), 1.96-1.82 (m, 1H), 1.21 (d, J=6.6 Hz, 3H). $^{13}$CNMR (126 MHz, DMSO-d$_6$) δ 170.49, 170.16 (d, J=2.52 Hz), 167.71, 160.33, 156.68 (d, J=241.92 Hz), 138.34, 134.57, 132.47, 130.40, 128.44, 128.12 (d, J=8.82 Hz), 126.81, 126.21, 121.43 (d, J=23.94 Hz), 116.12 (d, J=10.08 Hz), 107.10 (d, J=23.94 Hz), 96.61, 45.45, 42.14, 24.82, 22.08, 17.60. MS (ESI-TOF) for C$_{22}$H$_{20}$FN$_3$O$_4$[M+H]$^+$ calculated 410.1511; found, 410.1530.

9-Fluoro-7-hydroxy-3-methyl-N-((1-methyl-1H-pyrazol-5-yl)methyl)-5-oxo-2,3-dihydro-1H,5H-pyrido[3,2,1-ij]quinoline-6-carboxamide (41)

(1-Methyl-1H-pyrazol-5-yl)methanamine (13.34 mg, 0.12 mmol) was used as reagent. White solid (20 mg, 54%). $^1$H NMR (500 MHz, Chloroform-d) δ 16.51 (s, 1H), 10.77 (s, 1H), 7.75-7.68 (m, 1H), 7.42 (d, J=1.9 Hz, 1H), 7.25-7.20 (m, 1H), 6.28 (d, J=1.9 Hz, 1H), 6.29-5.15 (m, 1H), 4.75-4.59 (m, 2H), 3.91 (s, 3H), 3.23-3.10 (m, 1H), 2.93-2.82 (m, 1H), 2.13-2.05 (m, 1H), 2.03-1.92 (m, 1H), 1.28 (d, J=6.7 Hz, 3H). $^{13}$C NMR (126 MHz, CDCl$_3$) δ 170,91, 170.88, 161.42, 157.51 (d, J=244.44 Hz), 138.50, 138.37, 132.58, 127.08 (d, J=7.56 Hz), 121.44 (d, J=23.94 Hz), 117.29 (d, J=8.82 Hz), 108.58 (d, J=2394 Hz), 106.31, 97.38, 45.80, 36.79, 3383, 25.78, 2298, 18.08. MS (ESI-TOF) for C$_{19}$H$_{19}$FN$_4$O$_3$[M+H]$^+$ calculated 371.1514; found, 371.1565.

9-Fluoro-7-hydroxy-3-methyl-N-((1-methy-1H-pyrazol-4-yl)methyl)-5-oxo-2,3-dihydro-1H,5H-pyrido[3,2,1-ij]quinoline-6-carboxamide (42). (1-Methyl-1H-pyrazol-4-yl)methanamine (13.34 mg, 0.12 mmol) was used as reagent White solid (22 mg, 59%). $^1$H NMR (500 MHz, Chloroform-d) δ 16.91 (s, 1H), 10.59 (s, 1H), 7.75-7.69 (m, 1H), 7.49 (s, 1H), 7.41 (s, 1H), 7.24-7.18 (m, 1H), 5.27-5.18 (m, 1H), 4.56-4.41 (m, 2H), 3.88 (s, 3H), 3.24-3.08 (m, 1H), 2.91-2.82 (m, 1H), 2.12-2.04 (m, 1H), 2.02-1.92 (m, 1H), 1.27 (d, J=6.7 Hz, 3H). $^{13}$C NMR (126 MHz, CDCl$_3$) δ 170.98 (d, J=3.78 Hz), 170.80, 161.46, 157.48 (d, J=243.18 Hz), 138.98, 132.53, 129.48, 126.96 (d, J=7.56 Hz), 121.20 (d, J=23.94 Hz), 118.12, 117.52 (d, J=8.82 Hz), 108.58 (d, J=22.68 Hz), 97.48, 45.70, 39.12, 33.68, 25.82, 23.00, 18.09. MS (ESI-TOF) for C$_{19}$H$_{19}$FN$_4$O$_3$[M+H]$^+$ calculated 371.1514; found, 371.1527.

N-((1,3-Dimethyl-1H-pyrazol-4-yl)methyl)-9-fluoro-7-hydroxy-3-methyl-5-oxo-2,3-dihydro-1H,5H-pyrido[3,2,1-ij]quinoline-6-carboxamide (43)

(1,3-Dimethyl-1-pyrazol-4-yl)methanamine (15.02 mg, 0.12 mmol) was used as reagent. White solid (33 mg, 86%). $^1$H NMR (500 MHz, DMSO-d$_6$) δ 17.31 (s, 1H), 10.50 (t, J=5.5 Hz, 1H), 7.69-7.44 (m, 3H), 5.17-4.92 (m, 1H), 4.47-4.21 (m, 2H), 3.72 (s, 3H), 3.16-3.04 (m, 1H), 2.97-2.85 (m, 1H), 2.14 (s, 3H), 2.09-2.02 (m, 1H), 1.94-1.81 (m, 1H), 1.18 (d, J=6.6 Hz, 3H). $^{13}$C NMR (126 MHz, DMSO-d$_6$) δ 170.21 (d, J=3.78 Hz), 169.89, 160.35, 156.71 (d, J=241.92 Hz), 145.51, 132.42, 130.75, 128.16 (d, J=8.82 Hz), 121.41 (d, J=23.94 Hz), 116.19 (d, J=8.82 Hz), 114.56, 107.10 (d, J=23.94 Hz), 96.46, 45.44, 38.16, 32.49, 24.83, 22.10, 17.62, 11.35. MS (ESI-TOF) for C$_{20}$H$_{21}$FN$_4$O$_3$[M+H]$^+$ calculated 385.1670; found, 385.1704.

9-Fluoro-7-hydroxy-3-methyl-N-((1-methyl-1H-imidazol-2-yl)methyl)-5-oxo-2,3-dihydro-1H,5H-pyrido[3,2,1-ij]quinoline-6-carboxamide (44)

(1-Methyl-1H-imidazol-2-yl)methanamine (13.34 mg, 0.12 mmol) was used as reagent. White solid (34 mg, 92%). $^1$H NMR (500 MHz, DMSO-d$_6$) δ 10.90 (s, 1H), 7.68-7.48 (m, 2H), 7.13 (s, 1H), 6.84 (s, 1H), 5.20-5.02 (m, 1H), 4.73-4.53 (m, 2H), 3.65 (s, 3H), 3.20-3.03 (m, 1H), 2.93 (dd, J=17.1, 3.4 Hz, 1H), 2.13-2.02 (m, 1H), 1.96-1.79 (m, 1H), 1.21 (d, J=6.7 Hz, 3H). $^{13}$C NMR (126 MHz, DMSO-d$_6$) δ 170.21, 170.09, 16031, 156.73 (d, J:=240.66 Hz), 143.17, 132.52, 128.22 (d, J=7.56 Hz), 126.55, 122.11, 121.49 (d, J=23.94 Hz), 116.10 (d, J=7.56 Hz), 107.17 (d, J=23.94 Hz), 96.64, 45.49, 35.44, 32.22, 24.85, 22.12, 17.67. MS (ESI-TOF) for C$_{19}$H$_{19}$FN$_4$O$_3$ [M+H]$^+$ calculated 371.1514; found, 371.1563.

N-(2-(1H-Imidazol-1-yl)ethyl)-9-fluoro-7-hydroxy-3-methyl-5-oxo-2,3-dihydro-1H,5H-pyrido[3,2,1-ij]quinoline-6-carboxamide (45)

2-(1H-Imidazol-1-yl)ethanamine (13.34 mg, 0.12 mmol) was used as reagent. White solid (26 mg, 70%). $^1$H NMR (500 MHz, Chloroform-d) δ 16.41 (s, 1H), 10.65 (t, J=5.3 Hz, 1H), 7.74-7.67 (m, 1H), 7.52 (s, 1H), 7.25-7.20 (m, 1H), 7.09 (t, J=1.0 Hz, 1H), 6.99 (t, J=1.3 Hz, 1H), 5.27-5.16 (m, 1H), 4.30-4.15 (m, 2H), 3.87-3.67 (m, 2H), 3.24-3.09 (m, 1H), 2.88 (dd, J=16.9, 3.9 Hz, 1H), 2.13-1.91 (m, 2H), 1.28 (d, J=6.7 Hz, 3H). $^{13}$C NMR (126 MHz, CDCl$_3$) δ 171.71, 170.86 (d, J=2.52 Hz), 161.39, 157.50 (d, J=243.18 Hz), 137.50, 132.61, 130.14, 127.10 (d, J=7.56 Hz), 121.47 (d, J=23.94 Hz), 118.95, 117.25 (d, J=8.82 Hz), 108.58 (d, J=23.94 Hz), 97.29, 46.17, 45.81, 40.25, 25.78, 22.99, 18.07. MS (ESI-TOF) for C$_{19}$H$_{19}$FN$_4$O$_3$[M+H]$^+$ calculated 371.1514; found, 371.1626.

9-Fluoro-7-hydroxy-N-(isoxazol-5-ylmethyl)-3-methyl-5-oxo-2,3-dihydro-1H,5H-pyrido[3,2,1-ij]quinoline-6-carboxamide (46)

Isoxazol-5-yl-methylamine hydrochloride (16.15 mg, 0.12 mmol) was used as reagent. White solid (20 mg, 56%). $^1$H NMR (500 MHz, Chloroform-d) δ 16.30 (s, 1H), 10.96 (s, 1H), 8.21 (d, J=1.5 Hz, 1H), 7.72 (dd, J=8.6, 2.9 Hz, 1H), 7.24 (dd, J=8.3, 2.5 Hz, 1H), 6.30-6.22 (m, 1H), 5.30-5.20 (m, 1H), 4.85-4.73 (m, 2H), 3.27-3.07 (m, 1H), 2.89 (dd, J=16.9, 4.0 Hz, 1H), 2.15-2.05 (m, 1H), 2.04-1.91 (m, 1H), 1.30 (d, J=6.7 Hz, 3H). $^{13}$C NMR (126 MHz, CDCl$_3$) δ 171.42, 170.86 (d, J=2.52 Hz), 168.18, 161.43, 157.53 (d, J=244.44 Hz), 150.49, 132.65, 127.12 (d, J=7.56 Hz), 121.53 (d, J=23.94 Hz), 117.23 (d, J=8.82 Hz), 108.63 (d, J=23.94 Hz), 101.69, 97.46, 45.86, 34.90, 25.80, 22.99, 18.09. MS (ESI-TOF) for C$_{18}$H$_{16}$FN$_3$O$_4$[M+H]$^+$ calculated 358.1198; found, 358.1201.

9-Fluoro-7-hydroxy-3-methyl-N-((5-methylisoxazol-3-yl)methyl)-5-oxo-2,3-dihydro-1H,5H-pyrido[3,2,1-ij]quinoline-6-carboxamide (47)

(5-Methylisoxazol-3-yl)methanamine (13.45 mg, 0.12 mmol) was used as reagent. White solid (25 mg, 67%). $^1$H NMR (500 MHz, Chloroform-d) δ 16.53 (s, 1H), 10.87 (t, J=4.9 Hz, 1H), 7.75-7.69 (m, 1H), 7.25-7.19 (m, 1H), 6.05 (d, J=0.8 Hz, 1H), 5.32-5.20 (m, 1H), 4.76-4.52 (m, 2H), 3.25-3.08 (m, 1H), 2.88 (dd, J=17.0, 4.0 Hz, 1H), 2.40 (d, J=0.8 Hz, 3H), 2.12-2.05 (m, 1H), 2.02-1.92 (m, 1H), 1.28 (d, J=6.7 Hz, 3H). $^{13}$C NMR (126 MHz, CDCl$_3$) δ 171.40, 170.84 (d, J=3.78 Hz), 170.22, 161.41, 161.05, 157.49 (d, J=244.44 Hz), 132.62, 127.05 (d, J=7.56 Hz), 121.39 (d, J=23.94 Hz), 117.31 (d, J=8.82 Hz), 108.59 (d, J=23.94 Hz), 101.20, 97.49, 45.76, 35.13, 25.81, 23.00, 18.09, 12.47. MS (ESI-TOF) for C$_{19}$H$_{18}$FN$_3$O$_4$[M+H]$^+$ calculated 372.1354; found, 372.1454.

9-Fluoro-7-hydroxy-3-methyl-N-((5-methyl-1,3,4-oxadiazol-2-yl)methyl)-5-oxo-2,3-dihydro-1H,5H-pyrido[3,2,1-ij]quinoline-6-carboxamide (48)

(5-Methyl-1,3,4-oxadiazol-2-yl)methanamine (13.57 mg, 0.12 mmol) was used as reagent. White solid (19 mg, 51%).

¹H NMR (500 MHz, Chloroform-d) δ 11.03 (s, 1H), 7.72 (dd, J=8.4, 2.2 Hz, 1H), 7.25-7.21 (m, 1H), 5.32-5.21 (m, 1H), 4.92-4.76 (m, 2H), 3.24-3.08 (m, 1H), 2.88 (dd, J=16.9, 3.4 Hz, 1H), 2.54 (s, 3H), 2.13-1.91 (m, 2H), 1.30 (d, J=6.6 Hz, 3H). ¹³C NMR (126 MHz, CDCl₃) δ 171.55, 170.82 (d, J=3.78 Hz), 164.60, 163.30, 161.42, 157.54 (d, J=243.18 Hz), 132.71, 127.14 (d, J=7.56 Hz), 121.59 (d, J=23.94 Hz), 117.17 (d, J=8.82 Hz), 108.66 (d, J=22.68 Hz), 97.49, 45.88, 33.95, 25.82, 23.00, 18.09, 11.21. NM S (ESI-TOF) for C₁₈H₁₇FN₄O₄ [M+H]⁺ calculated 373.1307; found, 373.1353.

9-Fluoro-7-hydroxy-3-methyl-5-oxo-N-(thiophen-2-ylmethyl)-2,3-dihydro-1H,5H-pyrido[3,2,1-ij]quinoline-6-carboxamide (49)

2-Thiophenemethylamine (12.31 μL, 0.12 mmol) was used as reagent. White solid (25 mg, 67%). ¹H NMR (500 MHz, DMSO-d₆) δ 10.80 (t, J=5.9 Hz, 1H), 7.66-7.53 (m, 2H), 7.45 (dd, J=5.1, 1.2 Hz, 1H), 7.10 (dd, J=3.4, 1.1 Hz, 1H), 7.00 (dd, J=5.1, 3.5 Hz, 1H), 5.13-5.04 (m, 1H), 4.83-4.71 (m, 2H), 3.18-3.05 (m, 1H), 2.92 (dd, J=17.1, 3.3 Hz, 1H), 2.11-1.98 (m, 1H), 1.95-1.82 (m, 1H), 1.19 (d, J=6.6 Hz, 3H). ¹³C NMR (126 MHz, DMSO-d₆) δ 170.22, 170.17 (d, J=3.78 Hz), 160.26, 156.70 (d, J=240.66 Hz), 140.52, 132.51, 128.18 (d, J=7.56 Hz), 126.90, 126.57, 125.78, 121.52 (d, J=23.94 Hz), 116.05 (d, J=8.82 Hz), 107.13 (d, J=23.94 Hz), 96.54, 45.49, 37.11, 24.82, 22.10, 17.61. MS (ESI-TOF) for C₁₉H₁₇FN₂O₃S [M+H]⁺ calculated 373.1017; found, 373.1012.

9-Fluoro-7-hydroxy-3-methyl-5-oxo-N-(thiophen-3-ylmethyl)-2,3-dihydro-1,5-pyrido[3,2,1-ij]quinoline-6-carboxamide (50)

Thiophen-3-ylmethanamine (13.58 mg, 0.12 mmol) was used as reagent. White solid (27 mg, 73%). ¹H NMR (500 MHz, Chloroform-d) δ 16.88 (s, 1H), 10.75 (s, 1H), 7.76-7.68 (m, 1H), 7.31 (dd, J=5.0, 3.0 Hz, 1H), 7.25-7.19 (m, 2H), 7.11 (dd, J=5.0, 1.3 Hz, 1H), 5.29-5.20 (m, 1H), 4.73-4.58 (m, 2H), 3.23-3.10 (m, 1H), 2.88 (dd, J=16.9, 3.9 Hz, 1H), 2.13-2.03 (m, 1H), 2.02-1.92 (m, 1H), 1.28 (d, J=6.7 Hz, 3H). ¹³C NMR (126 MHz, CDCl₃) δ 170.99 (d, J=3.78 Hz), 170.92, 161.50, 157.48 (d, J=243.18 Hz), 138.51, 132.54, 127.47, 126.97 (d, J=7.56 Hz), 126.53, 122.45, 121,22 (d, J=23.94 Hz), 117.50 (d, J:=8.82 Hz), 108.59 (d, J=23.94 Hz), 97.49, 45.70, 38.46, 25.82, 23.01, MS (ESI-TOF) for C₁₉H₁₇FN₂O₃S [M+H]⁺ calculated 373.1017; found, 373.1039.

9-Fluoro-7-hydroxy-3-methyl-N-((1-methylpyrrolidin-3-yl)methyl)-5-oxo-2,3-dihydro-1H,5H-pyrido[3,2,1-ij]quinoline-6-carboxamide (51)

(1-Methylpyrrolidin-3-yl)methanamine (14.94 μL, 0.12 mmol) was used as reagent. White solid (22 mg, 59%). ¹H NMR (500 MHz, Chloroform-d) δ 17.00 (s, 1H), 10.54 (s, 1H), 7.72 (dd, J=8.5, 2.4 Hz, 1H), 7.21 (dd, J=8.3, 2.5 Hz, 1H), 5.31-5.18 (m, 1H), 3.56-3.36 (m, 2H), 3.22-3.11 (m, 1H), 2.94-2.76 (m, 2H), 2.71-2.52 (m, 3H), 2.40 (s, 4H), 2.15-2.05 (m, 2H), 2.04-1.93 (m, 1H), 1.67-1.56 (m, 1H), 1.29 (d, J=6.7 Hz, 3H). ¹³C NMR (126 MHz, CDCl₃) δ 171.22, 171.04, 161.56, 157.49 (d, J=243.18 Hz), 132.49, 126.96 (d, J=7.56 Hz), 121.17 (d, J 23.94 Hz), 117.59 (d, J=8.82 Hz), 108.58 (d, J=22.68 Hz), 97.36, 60.29, 56.05, 45.68, 43.37, 42.26, 38.03, 29.23, 25.82, 23.00, MS (ESI-TOF) for C₂₀H₂₄FN₃O₃[M+H]⁺ calculated 374.1874; found, 374.1951.

9-Fluoro-7-hydroxy-3-methyl-5-oxo-N-((tetrahydrofuran-3-yl)methyl)-2,3-dihydro-1H,5H-pyrido[3,2,1-ij]quinoline-6-carboxamide (52)

(Tetrahydrofuran-3-yl)methanamine (12.55 μL, 0.12 mmol) was used as reagent. Yellow solid (34 mg, 94%). ¹H NMR (500 MHz, DMSO-d₆) δ 17.32 (s, 1H), 10.55 (t, J=5.8 Hz, 1H), 7.73-7.45 (m, 2H), 5.21-5.05 (m, 1H), 3.81-3.69 (m, 2H), 3.63 (q, J=7.9 Hz, 1H), 3.51-3.36 (m, 3H), 3.18-3.06 (m, 1H), 2.93 (dd, J=17.1, 3.5 Hz, 1H), 2.59-2.52 (m, 1H), 2.13-2.04 (m, 1H), 2.02-1.84 (m, 2H), 1.67-1.55 (m, 1H), 1.21 (d, J=6.6 Hz, 3H). ¹³C NMR (126 MHz, DMSO-d₆) δ 170.64, 170.23 (d, J=2.52 Hz), 160.41, 156.70 (d, J=240.66 Hz), 132.44, 128.16 (d, J=7.56 Hz), 121.42 (d, J=23.94 Hz), 116.21 (d, J=8.82 Hz), 107.12 (d, J=23.94 Hz), 96.44, 70,35, 66.89, 45.45, 41.13, 38.58, 29.52, 24,84, 22.11, 17.65. MS (ESI-TOF) for C₁₉H₂₁FN₂O₄[M+H]⁺ calculated 361.1558; found, 361.1580.

N-Boc protected intermediates for compounds 53, 54, 56 and 57 were synthesized similarly as compound 2.

9-Fluorohydro-7-hydroxy-3-methyl-5-oxo-N-(piperidin-2-ylmethyl-2,3-dihydro-1H,5H-pyrido[3,2,1-ij]quinoline-6-carboxamide (53)

N-Boc protected intermediate. tert-Butyl 2-(aminomethyl)piperidine-1-carboxylate (25.41 μL, 0.12 mmol) was used as reagent. White solid (34 mg, 72%). ¹H NMR (500 MHz, Chloroform-d) δ 10.47 (s, 1H), 7.75-7.67 (m, 1H), 7.20 (d, J=8.0 Hz, 1H), 5.29-5.18 (m, 1H), 4.53 (s, 1H), 4.06 (s, 1H), 3.83-3.70 (m, 1H), 3.55-3.43 (m, 1H), 3.23-3.10 (m, 1H), 2.96-2.81 (m, 2H), 2.12-1.90 (m, 2H), 1.73-1.55 (m, 6H), 1.39 (d, J=4.1 Hz, 9H), 1.26 (d, J=6.5 Hz, 3H). ¹³C NMR (126 MHz, CDCl₃) δ 171.37, 170.89 (d, J=2.52 Hz), 161.33, 157.43 (d, J=243.18 Hz), 15516, 132.55, 126.86 (d, J=6.30 Hz), 121.10 (d, J=23.94 Hz), 117.49 (d, J=8.82 Hz), 108.57 (d, J=23.94 Hz), 97.42, 79.62, 45.58, 38.29, 28.44, 28.41, 26.61, 25.86, 25.50, 23.03, 19.42, 18.05, 18.03. MS (ESI-TOF) for C₂₅H₃₂FN₃O₅[M+H]⁺ calculated 474.2399; found, 474.2414.

Compound 53, N-Boc protected intermediate (23.68 mg, 0.05 mmol) was dissolved in hydrochloric acid (1 mL, 4 M in dioxane), and stirred at room temperature for 2 h. Excess solvent was removed under reduced pressure, and the resulting residue was thoroughly washed with diethyl ether and purified by flash chromatography (10% MeOH/DCM) to obtain the compound 53 as a white solid (16 mg, 86%). ¹H NMR (500 MHz, DMSO-d₆) δ 10.57 (s, 1H), 8.82 (s, 1H), 7.61 (dd, J=20.2, 8.6 Hz, 2H), 5.17-5.04 (m, 1H), 3.78-3.52 (m, 2H), 3.30-3.20 (m, 2H), 3.18-3.07 (m, 1H), 2.99-2.90 (m, 1H), 2.89-2.79 (m, 1H), 2.10 (d, J=13.2 Hz, 1H), 1.95-1.57 (m, 5H), 1.55-1.42 (m, 2H), 1.23 (d, J=6.4 Hz, 3H). ¹³C NMR (126 MHz, DMSO) δ 171.46, 169.84, 160.24, 156.74 (d, J=241.92 Hz), 132.41, 128.19 (d, J=7.56 Hz), 121.56 (d, J=22.68 Hz), 116.04 (d, J=6.30 Hz), 107.13 (d, J=25.2 Hz), 97.03, 55.47, 45.47, 44.02, 40.85, 25.95, 24.86, 22.06, 21.58, 21.32, 17.59. MS (ESI-TOF) for $C_{20}H_{24}FN_3O_3[M+H]^+$ calculated 374.1874; found, 374.1931.

Compound 54 was synthesized similarly as compound 53.

9-Fluoro-7-hydroxy-3-methyl-5-oxo-N-(piperidin-3-ylmethyl)-2,3-dihydro-1H,5H-pyrido[3,2,1-ij]quinoline-6-carboxamide (54)

N-Boc protected intermediate. tert-Butyl 3-(aminomethyl)piperidine-1-carboxylate (25.84 μL, 0.12 mmol) was used as reagent. White solid (32 mg, 68%). 1 NMR (500 MHz, Chloroform-d) δ 16.96 (s, 1H), 10.53 (s, 1H), 7.72 (dd, J=8.6, 2.6 Hz, 1H), 7.21 (dd, J=8.2, 2.6 Hz, 1H), 5.34-5.15 (m, 1H), 4.24-3.81 (m, 2H), 3.48-3.25 (m, 2H), 3.23-3.11 (m, 1H), 2.96-2.49 (m, 3H), 2.14-2.04 (m, 1H), 2.03-1.77 (m, 3H), 1.74-1.65 (m, 1H), 1.51-1.22 (m, 14H). $^{13}$C NMR (126 MHz, CDCl$_3$) δ 171.25, 170.97 (d, J=3.78 Hz), 161.54, 157.48 (d, J=243.18 Hz), 154.97, 132.50, 126.94 (d, J=7.56 Hz), 121.17 (d, J=23.94 Hz), 117.57 (d, J=7.56 Hz), 108.58 (d, J=23.94 Hz), 97.38, 79.62, 45.69, 42.10, 36.28, 28.81, 28.57, 25.84, 23.01, 18.09. MS (ESI-TOF) for $C_{25}H_{32}FN_3O_5[M+H]^+$ calculated 474.2399; found, 474.2405.

Compound 54. N-Boc protected intermediate (23.68 mg, 0.05 mmol) was used as reagent. White solid (17 mg, 91%). $^1$H NMR (500 MHz, Methanol-d$_4$) δ 7.68 (dd, J=8.7, 2.6 Hz, 1H), 7.41 (dd, J=8.6, 2.5 Hz, 1H), 5.30-5.17 (m, 1H), 3.46 (d, J=6.5 Hz, 2H), 3.44-3.32 (m, 2H), 3.28-3.18 (m, 1H), 3.00-2.89 (m, 2H), 2.80 (t, J=12.2 Hz, 1H), 2.22-1.91 (m, 5H), 1.82-1.69 (m, 1H), 1.47-1.36 (m, 1H), 1.30 (d, J=6.7 Hz, 3H). $^{13}$C NMR (126 MHz, MeOD) δ 172.59, 171.55 (d, J=: 3.78 Hz), 162.57, 158.93 (d, J=. 243.18 Hz), 133,84, 129.41 (d, J=7.56 Hz), 122.53 (d, J=23.94 Hz), 118.02 (d, J=8.82 Hz), 108.65 (d, J=25.20 Hz), 98.32, 48.26, 47.33, 45.37, 42.34, 35.90, 27.42, 26.59, 23.58, 23.04, 18.00. MS (ESI-TOF) for $C_{20}H_{24}FN_3O_3[M+H]^+$ calculated 374.1874; found, 374.1931.

Compound 55 was synthesized similarly as compound 2.

9-Fluoro-7-hydroxy-3-methyl-N-((1-methylpiperidin-3-yl)methyl)-5-oxo-2,3-dihydro-1H,5H-pyrido[3,2,1-ij]quinoline-6-carboxamide (55)

(1-Methylpiperidin-3-yl)methanamine (17.08 μL, 0.12 mmol) was used as reagent. White solid (36 mg, 93%). $^1$H NMR (500 MHz, Chloroform-d) δ 10.48 (s, 1H), 7.71 (d, J=7.9 Hz, 1H), 7.20 (d, J=7.4 Hz, 1H), 5.34-5.16 (m, 1H), 3.44-3.26 (m, 2H), 3.22-3.11 (m, 1H), 2.87 (d, J=12.4 Hz, 2H), 2.77 (d, J=10.3 Hz, 1H), 2.27 (s, 3H), 2.13-1.87 (m, 4H), 1.85-1.68 (m, 3H), 1.67-1.55 (m, 1H), 1.29 (d, J=6.6 Hz, 3H), 1.09-0.96 (m, 1H). $^{13}$C NMR (126 MHz, CDCl$_3$) 171.18, 171.04 (d, J=2:52 Hz), 161.56, 157.47 (d, J=243.18 Hz), 132.49, 126.92 (d, J=6.30 Hz), 121.12 (d, J-=23.94 Hz), 117.63 (d, J=8.82 Hz), 108.57 (d, J=23.94 Hz), 97.38, 60.16, 56.25, 46.83, 45.67, 42.90, 36.71, 28.21, 25.83, 25.09, 23.01, 18.12. MS (ESI-TOF) for $C_{21}H_{26}FN_3O_3[M+H]^+$ calculated 388.2031; found, 388.2106.

Compounds 56 and 57 were synthesized similarly as compound 53.

9-Fluoro-7-hydroxy-3-methyl-5-oxo-N-(piperidin-4-ylmethyl)-2,3-dihydro-1H,5H-pyrido[3,2,1-ij]quinoline-6-carboxamide hydrochloride (56)

N-Boc protected intermediate. tert-Butyl 4-(aminomethyl)piperidine-1-carboxylate (25.72 mg, 0.12 mmol) was used as reagent. White solid (30 mg, 63%). $^1$H NMR (500 MHz, DMSO-d$_6$) δ 17.37 (s, 1H), 10.53 (t, J=6.0 Hz, 1H), 7.83-7.37 (m, 2H), 5.11 (s, 1H), 4.08-3.84 (m, 2H), 3.30-3.23 (m, 1H), 3.17-3.05 (m, 1H), 2.93 (dd, J=17.1, 3.4 Hz, 1H), 2.85-2.57 (m, 3H), 2.11-2.02 (m, 1H), 1.95-1.84 (m, 1H), 1.81-1.70 (m, 1H), 1.65 (d, J=12.2 Hz, 2H), 1.39 (s, 9H), 1.21 (d, J=6.6 Hz, 3H), 1.14-1.02 (m, 2H). $^{13}$C NMR (126 MHz, DMSO-d$_6$) δ 170.54, 170.24 (d, J=3.78 Hz), 160.46, 156.70 (d, J=240.66 Hz), 153.87, 132.40, 128.16 (d, J=8.82 Hz), 121.40 (d, J=23.94 Hz), 116.24 (d, J=8.82 Hz), 107.11 (d, J=23.94 Hz), 96.42, 78.53, 54.95, 45.45, 43.73, 35.51, 29.31, 28.10, 24.84, 22.10, 17.64. MS (ESI-TOF) for $C_{25}H_{32}FN_3O_5[M+H]^+$ calculated 474.2399; found, 474.2411.

Compound 56. N-Boc protected intermediate (23.68 mg, 0.05 mmol) was used as reagent. White solid (15 mg, 80%0). $^1$H NMR (500 MHz, DMSO-d$_6$) δ 10.53 (t, J=5.6 Hz, 1H), 9.00 (s, 1H), 8.64 (s, 1H), 7.59 (dd, J=17.3, 8.6 Hz, 2H), 5.17-5.02 (m, 1H), 3.42-3.34 (m, 1H), 3.31-3.22 (m, 3H), 3.17-3.05 (m, 1H), 2.98-2.79 (m, 3H), 2.08 (d, J=13.5 Hz, 1H), 1.97-1.74 (m, 4H), 1.50-1.35 (m, 2H), 1.21 (d, J=6.5 Hz, 3H). $^{13}$C NMR (126 MHz, CDCl$_3$) δ 171.43, 170.98 (d, J=2.52 Hz), 161.54, 157.52 (d, J=244.44 Hz), 132.52, 127.03 (d, J=7.56 Hz), 121.35 (d, J=23.94 Hz), 117.46 (d, J=7.56 Hz), 108.60 (d, J=23.94 Hz), 97.34, 45.78, 43.80, 43.75, 34.61, 29.85, 26.88, 26.85, 25.82, 22.99, 18.11. MS (ESI-TOF) for $C_{20}H_{24}FN_3O_3[M+H]^+$ calculated 374.1874; found, 374.1919.

9-Fluoro-7-hydroxy-3-methyl-N-(morpholin-2-ylmethyl)-5-oxo-2,3-dihydro-1H,5H-pyrido[3,2,1-ij]quinoline-6-carboxamide (57)

N-Boc protected intermediate, tert-Butyl 2-(aminomethyl)morpholine-4-carboxylate (25.95 mg, 0.12 mmol) was used as reagent. White solid (42 mg, 88%). $^1$H NMR (500 MHz, Chloroform-d) δ 16.80 (s, 1H), 10.60 (s, 1H), 7.71 (dd, J=8.6, 2.7 Hz, 1H), 7.21 (dd, J=8.3, 2.5 Hz, 1H), 5.30-5.23 (m, 1H), 4.16-3.34 (m, 8H), 3.25-3.08 (m, 1H), 3.04-2.61 (m, 3H), 2.11-2.05 (m, 1H), 2.02-1.92 (m, 1H), 1.46 (s, 9H), 1.29 (dd, J=6.6, 1.9 Hz, 3H). $^{13}$C NMR (126 MHz, CDCl$_3$) δ 171.33, 170.90 (d, J=3.78 Hz), 161.45, 157.46 (d, J=243.18 Hz), 154.81, 132.58, 126.94 (d, J=7.56 Hz), 121.22 (d, J=23.94 Hz), 117.46 (d, J=8.82 Hz), 108.58 (d, J=23.94 Hz), 97.47, 80.33, 74.06, 66.70, 45.64, 41.28, 28.52, 25.82, 23.01, 18.12. MS (ESI-TOF) for $C_{24}H_{30}FN_3O_6[M+H]^+$ calculated 476.2191; found, 476.2186.

Compound 57. N-Boc protected intermediate (23.77 mg, 0.12 mmol) was used as reagent. White solid (30 mg, 80%). $^1$H NMR (500 MHz, Methanol-d$_4$) δ 7.66 (dd, J=8.8, 2.9 Hz, 1H), 7.38 (dd, J=8.6, 2.5 Hz, 1H), 5.30-5.15 (m, 1H), 3.99-3.90 (m, 1H), 3.76-3.55 (m, 3H), 3.46-3.36 (m, 1H), 3.27-3.16 (m, 1H), 3.01-2.81 (m, 4H), 2.70-2.58 (m, 1H), 2.20-2.08 (m, 1H), 2.06-1.93 (m, 1H), 1.29 (d, J=6.6 Hz, 3H). $^{13}$C NMR (126 MHz, DMSO-d$_6$) δ 170.65 (d, J=7.56 Hz), 170.26, 160.48, 156.71 (d, J=241.92 Hz), 132.39, 128.15 (d, J=8.82 Hz), 121.40 (d, J=8.82 Hz), 116.41 (d, J=3.78 Hz), 107.15 (d, J=22.68 Hz), 96.34, 72.35, 64.39, 45.74, 45.43, 43.14, 40.75, 24.83, 22.07, 17.62. MS (ESI-TOF) for $C_{19}H_{22}FN_3O_4[M+H]^+$ calculated 376.1667; found, 376.1717.

Example 4

The following representative compounds of the invention were also prepared as described by Hu Z, et al., ACS Med. Chem. Lett., 2019, 10, 132-136.

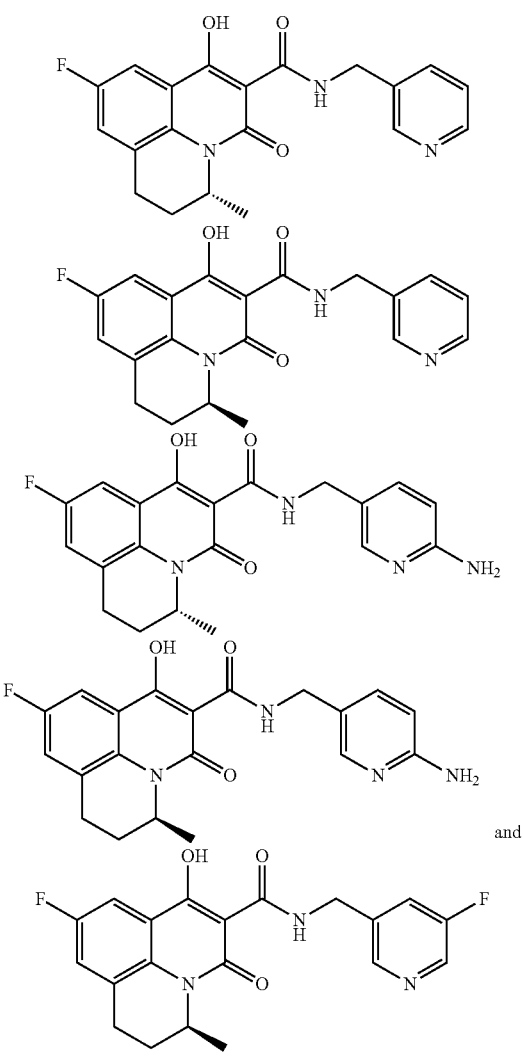

and

Example 5

The biological activity of compounds of the invention can be evaluated using the following assays:

TLR2-Specific NF-κB Induction (Reporter Gene Assay).

The induction of NF-κB in a TLR2-specific reporter gene assay was quantified using HEK-Blue™ cells as previously described by us. HEK293 cells stably transfected with human TLR2 and alkaline phosphatase (sAP) were obtained from InvivoGen (San Diego, Calif.), and were maintained in HEK-Blue™ Selection medium containing zeocin and normocin. Stable expression of secreted alkaline phosphatase (sAP) under control of NF-κB promoters is inducible by TLR2 agonists, and extracellular sAP in the supernatant is proportional to NF-κB induction. HEK-Blue cells were incubated at a density of ~105 cells/mL in a volume of 80 µL/well, in 384-well, flat-bottomed, cell culture-treated microtiter plates until confluency was achieved, and then stimulated with serially-diluted aliquots of compounds for 12 h. sAP was assayed spectrophotometrically using an alkaline phosphatase-specific chromogen (present in the HEK-detection medium as supplied by the vendor) at 620 nm.

Immunoassays for Cytokines and Chemokines.

Human embryonic kidney (HEK) cell stably transfected with human TLR2 were stimulated with graded concentrations of test compounds. Supernatants were harvested by centrifugation, and MCP-1 ELISAs were from performed according to manufacturer's instructions (R&D Biosystems, Minneapolis, Minn.). Supernatants from THP-1 cells stimulated with graded concentrations of test compounds were isolated by centrifugation, and were assayed in triplicates using analyte-specific multiplexed cytokine/chemokine bead array assays (Milliplex HCYTOMAG-60K, EMD Millipore, Billerica, Mass.) as reported by us previously. The analytes examined include: sCD40L, VEGF, TNF-β, TNF-α, TGF-α, RANTES, PDGF-AB/BB, PDGF-AA, MIP-1β, MIP-1α, MDC (CCL22), MCP-3, MCP-1, IP-10, IL-17A, IL-15, IL-13, IL-12 (p70), IL-12 (p40), IL-10, IL-9, IL-8, IL-7, IL-6, IL-5, IL-4, IL-3, IL-2, IL-1ra, IL-1β, IL-1α, IFN-γ, IFN-α2, GRO, GM-CSF, G-CSF, Fractalkine, Flt-3 ligand, FGF-2, Eotaxin, EGF.

Biological data for representative compounds of the invention was reported by Hu Z, et al., ACS Med. Chem. Lett., 2019, 10, 132-136.

Example 6

The following illustrate representative pharmaceutical dosage forms, containing a compound of formula I ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X= (free acid form) | 1.0 |
| Dibasic sodium phosphate | 12.0 |
| Monobasic sodium phosphate | 0.7 |

| (iv) Injection 1 (1 mg/ml) | mg/ml |
|---|---|
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X= (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents (including Hu Z, et al., ACS Med. Chem. Lett., 2019, 10, 132-136) are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

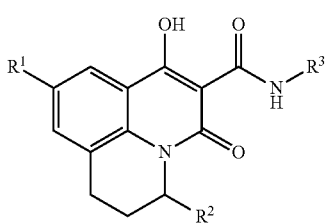

wherein:
$R^1$ is F;
$R^2$ is methyl;
$R^3$ is 2,3-cyclopentenopyridine.

2. A compound of formula I:

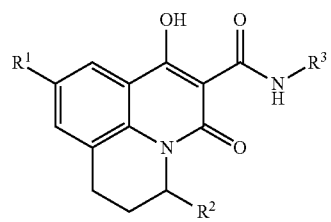

wherein:
$R^1$ is F;
$R^2$ is methyl;
$R^3$ is $(C_1-C_6)$alkyl that is substituted with:

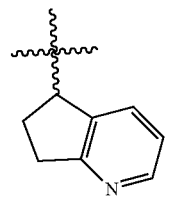

that is optionally substituted with one or more groups independently selected from alkyl, hydroxy, halogen, aryl, heteroayl, —$NR^aR^b$, —$C(=O)NR^aR^b$, —$CF_3$, $(C_2-C_6)$alkanoyloxy, $(C_1-C_6)$alkanoyl, $(C_1-C_6)$alkoxycarbonyl, and $(C_1-C_6)$alkoxy;
  each $R^a$ and $R^b$ is independently selected from the group consisting of H and $(C_1-C_6)$alkyl; or $R^a$ and $R^b$ together with the nitrogen to which they are attached form a aziridino, azetidino, morpholino, piperazino, pyrrolidino, imidazole, or piperidino.

* * * * *